US011172869B2

(12) United States Patent
Johnson et al.

(10) Patent No.: US 11,172,869 B2
(45) Date of Patent: Nov. 16, 2021

(54) NON-INVASIVE SYSTEM AND METHOD FOR PRODUCT FORMULATION ASSESSMENT BASED ON PRODUCT-ELICITED BRAIN STATE MEASUREMENTS

(71) Applicant: HI LLC, Los Angeles, CA (US)

(72) Inventors: Bryan Johnson, Culver City, CA (US); Husam Katnani, Braintree, MA (US); Daniel Sobek, Portola Valley, CA (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/853,614

(22) Filed: Apr. 20, 2020

(65) Prior Publication Data

US 2020/0337624 A1 Oct. 29, 2020

Related U.S. Application Data

(60) Provisional application No. 62/839,405, filed on Apr. 26, 2019, provisional application No. 62/894,578, filed on Aug. 30, 2019.

(51) Int. Cl.
*A61B 5/00* (2006.01)
*G16H 20/90* (2018.01)
(Continued)

(52) U.S. Cl.
CPC ............ *A61B 5/4064* (2013.01); *A61B 5/165* (2013.01); *A61B 5/6803* (2013.01); *G16H 20/10* (2018.01);
(Continued)

(58) Field of Classification Search
CPC ... A61B 5/04847; A61B 5/4064; A61B 5/375; A61B 5/377; A61B 5/378; A61B 5/38; A61B 5/381
See application file for complete search history.

(56) References Cited

U.S. PATENT DOCUMENTS 5,377,100 A 12/1994 Pope et al.
5,720,619 A 2/1998 Fisslinger
(Continued)

FOREIGN PATENT DOCUMENTS

WO WO02043564 6/2002
WO WO2012135068 10/2012
(Continued)

OTHER PUBLICATIONS

PCT International Search Report and Written Opinion for International Appln. No. PCT/US2020/025971, Applicant HI LLC, forms PCT/ISA/210, 220 and 237 dated Sep. 15, 2020 (15 pages).
(Continued)

*Primary Examiner* — Puya Agahi
(74) *Attorney, Agent, or Firm* — Michael J. Bolan; Vista IP Law Group, LLP

(57) ABSTRACT

A non-invasive product customization system and a method of customizing a product formulation is provided. Brain activity of a user is detected in response to an input of a product formulation into a brain of the user via a sensory nervous system of the user. A mental state of the user is detected based on the detected brain activity. The product formulation is modified based on the determined mental state of the user. The modified product formulation may be presented to the user in a manner that modulates the mental state of the user.

26 Claims, 14 Drawing Sheets

(51) Int. Cl.
    *G16H 20/10*     (2018.01)
    *A61B 5/16*     (2006.01)
    *A61B 5/381*     (2021.01)
    *A61B 5/377*     (2021.01)
    *A61B 5/38*     (2021.01)
    *A61B 5/375*     (2021.01)
    *A61B 5/378*     (2021.01)

(52) U.S. Cl.
    CPC .............. *G16H 20/90* (2018.01); *A61B 5/375* (2021.01); *A61B 5/377* (2021.01); *A61B 5/378* (2021.01); *A61B 5/38* (2021.01); *A61B 5/381* (2021.01); *A61B 2562/0223* (2013.01); *A61B 2562/0238* (2013.01)

(56) References Cited

U.S. PATENT DOCUMENTS

| | | | |
|---|---|---|---|
| 5,853,370 | A | 12/1998 | Chance et al. |
| 6,231,187 | B1 | 5/2001 | Munoz |
| 6,488,617 | B1 | 12/2002 | Katz |
| 8,209,224 | B2 | 6/2012 | Pradeep et al. |
| 8,473,024 | B2 | 6/2013 | Causevic et al. |
| 8,609,162 | B2 | 12/2013 | Giuliano et al. |
| 8,762,202 | B2 | 6/2014 | Pradeep et al. |
| 9,101,279 | B2 | 8/2015 | Ritchey et al. |
| 9,114,140 | B2 | 8/2015 | Giuliano et al. |
| 9,265,974 | B2 | 2/2016 | You et al. |
| 9,339,227 | B2 | 5/2016 | Darcy et al. |
| 9,417,106 | B2 | 8/2016 | Tobita |
| 9,440,064 | B2 | 9/2016 | Wingeier et al. |
| 9,704,205 | B2 | 7/2017 | Akutagawa et al. |
| 9,712,736 | B2 | 7/2017 | Kearns et al. |
| 9,729,252 | B2 | 8/2017 | Tyler et al. |
| 9,736,603 | B2 | 8/2017 | Osborne et al. |
| 9,943,698 | B2 | 4/2018 | Chase et al. |
| 9,946,344 | B2 | 4/2018 | Ayaz et al. |
| D817,553 | S | 5/2018 | Aaskov et al. |
| D825,112 | S | 8/2018 | Saez |
| 10,091,554 | B1 | 10/2018 | Newell et al. |
| 10,143,414 | B2 | 12/2018 | el Kaliouby et al. |
| 10,188,860 | B2 | 1/2019 | Wingeier et al. |
| 10,234,942 | B2 | 3/2019 | Connor |
| 10,258,760 | B1 | 4/2019 | Sherpa et al. |
| 2003/0176806 | A1 | 9/2003 | Pineda et al. |
| 2004/0049134 | A1 | 3/2004 | Tosaya et al. |
| 2005/0273017 | A1 | 12/2005 | Gordon |
| 2006/0150989 | A1 | 7/2006 | Migaly |
| 2006/0161218 | A1 | 7/2006 | Danilov |
| 2008/0177197 | A1 | 7/2008 | Lee et al. |
| 2009/0083129 | A1 | 3/2009 | Pradeep et al. |
| 2012/0172743 | A1 | 7/2012 | Aguilar et al. |
| 2013/0211238 | A1* | 8/2013 | DeCharms ............ A61B 5/0042 600/418 |
| 2013/0289385 | A1 | 10/2013 | Lozano et al. |
| 2013/0297599 | A1 | 11/2013 | Henshall |
| 2013/0311132 | A1 | 11/2013 | Tobita |
| 2014/0023999 | A1 | 1/2014 | Greder |
| 2014/0200432 | A1 | 7/2014 | Banerji et al. |
| 2014/0228701 | A1 | 8/2014 | Chizeck et al. |
| 2014/0303450 | A1 | 10/2014 | Caponi |
| 2014/0347265 | A1* | 11/2014 | Aimone ................ G02C 11/10 345/156 |
| 2015/0248651 | A1 | 9/2015 | Akutagawa et al. |
| 2015/0290454 | A1 | 10/2015 | Tyler et al. |
| 2015/0297109 | A1 | 10/2015 | Garten |
| 2015/0338917 | A1 | 11/2015 | Steiner et al. |
| 2015/0355462 | A1 | 12/2015 | Saito et al. |
| 2016/0077547 | A1 | 3/2016 | Aimone |
| 2016/0220163 | A1 | 8/2016 | Yamada |
| 2016/0242690 | A1 | 8/2016 | Principe et al. |
| 2016/0270656 | A1 | 9/2016 | Samec et al. |
| 2017/0035317 | A1* | 2/2017 | Jung ...................... A61B 5/161 |
| 2017/0042439 | A1 | 2/2017 | Yeow |
| 2017/0188876 | A1 | 7/2017 | Marci et al. |
| 2017/0202518 | A1 | 7/2017 | Furman et al. |
| 2017/0229037 | A1 | 8/2017 | Gazzaley |
| 2017/0262943 | A1 | 9/2017 | Akutagawa et al. |
| 2017/0347906 | A1 | 12/2017 | Intrator |
| 2017/0352283 | A1 | 12/2017 | Lau |
| 2018/0092557 | A1 | 4/2018 | Bickford et al. |
| 2018/0160982 | A1* | 6/2018 | Laszlo ................ A61B 5/7225 |
| 2018/0278984 | A1 | 9/2018 | Aimone |
| 2018/0348863 | A1* | 12/2018 | Aimone ............... A61B 5/6803 |
| 2019/0021657 | A1 | 1/2019 | Mohammadrezazadeh et al. |
| 2019/0082990 | A1 | 3/2019 | Poltorak |
| 2019/0200888 | A1 | 7/2019 | Poltorak |
| 2019/0201691 | A1 | 7/2019 | Poltorak |
| 2019/0224441 | A1 | 7/2019 | Poltorak |
| 2019/0246929 | A1 | 8/2019 | Poltorak |
| 2019/0247662 | A1 | 8/2019 | Poltorak |
| 2019/0321583 | A1 | 10/2019 | Poltorak |
| 2020/0196932 | A1* | 6/2020 | Johnson ............... A61B 5/0022 |

FOREIGN PATENT DOCUMENTS

| | | |
|---|---|---|
| WO | WO2014055932 | 4/2014 |
| WO | 2939706 | 11/2015 |
| WO | WO2016022414 | 2/2016 |
| WO | WO2019104008 | 5/2019 |

OTHER PUBLICATIONS

Judith Amores, et al., "Promoting Relaxation Using Virtual Reality, Olfactory Interfaces and Wearable EEG," 2018 IEEE 15th International Conference on Waerable and Implantable Body Sensor Networks; Mar. 4, 2018, (4 pages).

PCT International Search Report and Written Opinion for International Appln. No. PCT/US2020/029031, Applicant HI LLC, forms PCT/ISA/210, 220 and 237 dated Sep. 2, 2020 (18 pages).

Final Office Action dated Jul. 29, 2020, 27 pages.

PCT International Search Report and Written Opinion for International Appln. No. PCT/US2019/024027, Applicant HI LLC, forms PCT/ISA/210, 220 and 237 dated Aug. 19, 2019 (13 pages).

Lee, B.T., Seok, J.H., Lee., B.C, Cho, S.W., Chai, J.H., Choi, I.G., Ham, B.J., "Neural correlates of affective processing in response to sad and angry facial stimuli in patients with major depressive disorder," Prog Neuropsychopharmacol Biol Psychiatry, 32(3), 778-85 (2008.

A.C. Felix-Ortiz, A.C., Burgos-Robles, A., Bhagat, N.D., Leppla, C.A., Tye, K.M., "Bidirectional modulation of anxiety-related and social behaviors by amygdala projections to the medial prefrontal cortex," Neuroscience 321, 197-209 (2016).

Beauregard, M., Levesque, J. & Bourgouin, P., "Neural correlates of conscious self-regulation of emotion," J. Neurosci. (2001): 21, RC165.

Phan, K. L., Wager, T., Taylor, S. F. & Liberzon, I., "Functional neuroanatomy of emotion: a meta-analysis of emotion activation studies in PET and fMRI," Neuroimage, 16, 331-348 (2002).

Canli, T. & Amin, Z., "Neuroimaging of emotion and personality: scientific evidence and ethical considerations," Brain Cogn., 50, 414-431 (2002).

McCloskey, M. S., Phan, K. L. & Coccaro, E. F., "Neuroimaging and personality disorders," Curr. Psychiatry Rep., 7, 65-72 (2005).

Heekeren, H. R., Marrett, S., Bandettini, P. A. & Ungerleider, L. G., "A general mechanism for perceptual decision-making in the human brain," Nature, 431, 859-862 (2004).

Shin LM, Rauch SL, Pitman RK., "Amygdala, Medial Prefrontal Cortex, and Hippocampal Function in PTSD," Ann N Y Acad Sci., 1071(1) (2006).

Lis E, Greenfield B, Henry M, Guile JM, Dougherty G., "Neuroimaging and genetics of borderline personality disorder: a review," J Psychiatry Neurosci., 32(3), 162-173 (2007).

Etkin A, Wager TD, "Functional neuroimaging of anxiety: a meta-analysis of emotional processing in PTSD, social anxiety disorder, and specific phobia," Am J Psychiatry, 164(10),1476-1488 (2007).

Hamilton, P., Etkin A., "Functional Neuroimaging of Major Depressive Disorder: A Meta-Analysis and New Integration of Baseline Activation and Neural Response Data", Am J Psychiatry, 169(7), 693-703 (2012).

(56) References Cited

OTHER PUBLICATIONS

Sheline YI, Price JL, Yan Z, Mintun MA, "Resting-state functional MRI in depression unmasks increased connectivity between networks via the dorsal nexus," Proc Natl Acad Sci., 107(24), 11020-11025 (2010).
Bari A, Robbins TW, "Inhibition and impulsivity: Behavioral and neural basis of response control," Prog Neurobiol., 108:44-79 (2013).
Kagias, Konstantinos et al. "Neuronal responses to physiological stress," Frontiers in genetics, 3:222 (2012).
Clark, Ian A., et al., "First steps in using machine learning on fMRI data to predict intrusive memories of traumatic film footage", 0005-7967/ 2014 The Authors. Published by Elsevier Ltd. Behaviour Research and Therapy. This is an open access article under the CC BY license (http://creativecommons.org/licenses/by/3.0/); 10 pgs.
George, Mark S., M.D., "Changes in Mood and Hormone Levels After Rapid-Rate Transcranial Magnetic Stimulation (rTMS) of the Prefrontal Cortex", Journal of Neuropsychiatry, vol. 8, No. 2, Spring 1996, 9 pages.
Milad, M. R., et al., "Neuroscience of fear extinction: Implications for assessment and treatment of fear-based and anxiety related disorders", Behaviour Research and Therapy (2014), http://dx.doi.org/10.1016/j.brat.2014.08.006, 7 pages.
S.Z.K, Tan et al.,"Eternal sunshine of the neuromodulated mind: Altering fear memories through neuromodulation", Experimental Neurology 314 (2019) 9-19, 11 pages.
Zhang, Fei-Fei, et al., "Brain structure alterations in depression: Psychoradiological evidence", CNS Neurosci T 2018, John Wiley & Sons Ltd her. 2018;24:994-1003, 10 pages.
Non-Final Office Action dated Oct. 4, 2019, 26 pages.
Amendment and response filed Nov. 8, 2019, 11 pages.
Final Office Action dated Jan. 27, 2020, 21 pages.
Amendment and response filed Feb. 26, 2020, 14 pages.
Non-Final Office Action dated Mar. 23, 2020, 15 pages.
PCT International Search Report and Written Opinion for International Appln. No. PCT/US2019/043768, Applicant HI LLC, forms PCT/ISA/210, 220 and 237 dated Oct. 15, 2019 (11 pages).
Marianna Papadopoulou et al.; "Event-related potentials before saccades and antisaccades and their relation to reaction time", Experimental Brain Research, Springer, Berlin, DE, vol. 205, No. 4, Aug. 14, 2010, pp. 521-531, XP019840052.
Frank Schmal et al., "Effect of Ethanol on Visual-Vestibular Interactions During Vertical Linear Body Acceleration", Alcoholism: Clinical and Experimental Research, vol. 27, No. 9, Sep. 1, 2003, pp. 1520-1526, XP055626675.
Stefan K. Ehrlich, et al., "A closed-loop, music-based brain-computer interface for emotion mediation," PLoS ONE 14(3): e0213516. https://doi.org/10.1371/journal.pone.0213516; Mar. 18, 2019.
Patrick Gomez, et al., "Relationships Between Musical Structure and Psychophysiological Measures of Emotion", American Psychological Association, vol. 7, No. 2, 2007, pp. 377-387, 10 pages.
Fernando Lopes da Silva, "EEG and MEG: Relevance to Neuroscience", Center of Neuroscience; http://dx.doi.org/10.1016/j.neuron.2013.10.017; 17 pages.
Elena Boto, et al., "A new generation of magnetoencephalography: Room temperature measurements using optically-pumped magnetometers", NeuroImage 149 (2017) 404-414; 11 pages.
Stanislas Dehaene, et al., "Imaging unconscious semantic priming", Nature; vol. 395; Oct. 8, 1998; 4 pages.
John D. E. Gabrieli, et al., "The role of left prefrontal cortex in language and memory". Proc. Natl. Acad. Sci. USA, vol. 95, pp. 906-913, Feb. 1998; 8 pages.
Yang Jiang, et al., "Turning up the Old Brain with New Tricks: Attention Training via Neurofeedback", Frontiers in Aging Neuroscience; Mar. 2017; vol. 9; Article 52; 9 pages.
Peter Lintelle, Sensory Marketing Aspects: Priming, Expectations, Crossmodal Correspondences & More; CreateSpace Independent Publishing Platform, Jul. 23, 2014, ISBN-10: 1500616400, ISBN-13: 978-1500616403; 3 pages.
Samat Moldakarimova, et al., "Perceptual priming leads to reduction of gamma frequency oscillations", PNAS, Mar. 23, 2010, vol. 107, No. 12; 6 pages.
M. Teplan, "Fundamentals of EEG Measurement", Measurement Science Review, vol. 2, Section 2, 2002; 11 pages.
PCT International Search Report and Written Opinion for International Appln. No. PCT/US2020/034831, Applicant HI LLC, forms PCT/ISA/210 and 237 dated Feb. 8, 2021 (18 pages).

\* cited by examiner

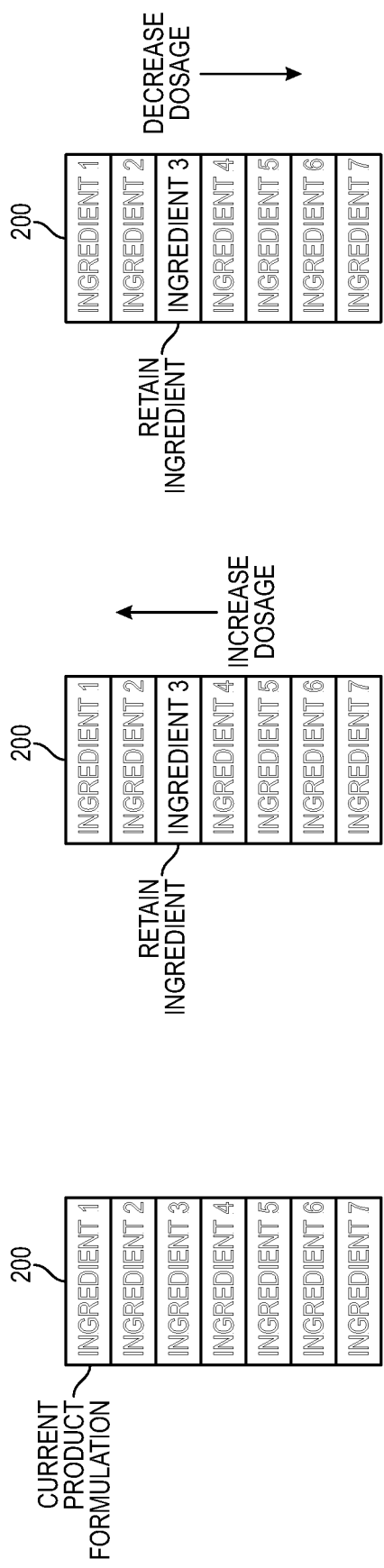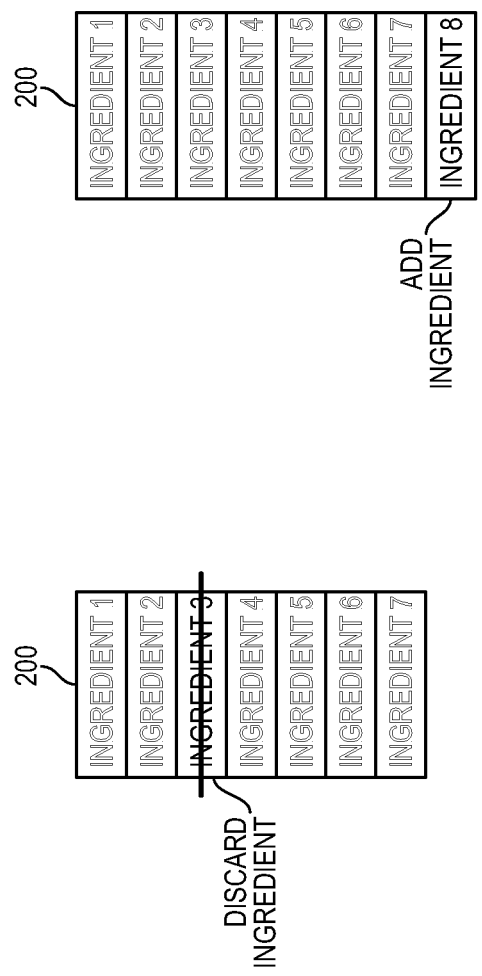

NON-INVASIVE SYSTEM AND METHOD FOR PRODUCT FORMULATION ASSESSMENT BASED ON PRODUCT-ELICITED BRAIN STATE MEASUREMENTS

RELATED APPLICATION DATA

Pursuant to 35 U.S.C. § 119(e), this application claims the benefit of U.S. Provisional Application Ser. No. 62/839,405, filed Apr. 26, 2019, and U.S. Provisional Application Ser. No. 62/894,578, filed Aug. 30, 2019, which are expressly incorporated herein by reference.

FIELD OF THE INVENTION

The present inventions relate to methods and systems for non-invasive measurements in the human body, and in particular, methods and systems related to detecting a mental state of a human.

BACKGROUND OF THE INVENTION

There exist businesses that create personalized products, such as, e.g., fragrances, homeopathic oils, lotions, food, drinks, psychotropic substances, etc. Typically, the formulations for such personalized products are created by providing sensory input in the form of a different product formulization to a person and receiving voluntary sensory feedback from the person to different formulations of the product. However, the voluntary sensory feedback provided by any particular person will only be as accurate as the sensory limitations of that person. For example, sometimes a person may be inconsistent or intentionally untruthful in his or her voluntary sensory feedback to the formulations of the product, or may not have full conscious awareness of his or her reaction to the sensory input. Thus, the voluntary sensory feedback provided by any particular person may not be a reliable indicator that a particular product formulization is properly personalized to that person.

There, thus, remains a need to personalize product formulations to a particular person without relying on the voluntary sensory feedback from such person.

SUMMARY OF THE INVENTION

In accordance with a first aspect of the present inventions, a non-invasive product customization system comprises a non-invasive brain interface assembly configured for detecting brain activity of a user (e.g., while the user is in a normal life and work environment) in response to an input of a product formulation (e.g., one or more of a fragrance, homeopathic oil for external therapeutic applications, lotion, food, drink, and psychotropic substances) into a brain of the user via a sensory nervous system (e.g., olfactory sensory system and/or gustatory sensory system) of the user. In one embodiment, the non-invasive brain interface assembly is an optical measurement assembly. In another embodiment, the non-invasive brain interface assembly is a magnetic measurement assembly. The non-invasive brain interface assembly may comprise, e.g., at least one detector configured for detecting energy from a brain of the user, and processing circuitry configured for identifying the brain activity in response to detecting the energy from the brain of the user. The non-invasive brain interface assembly may comprise a head-worn unit carrying the at least one detector, and an auxiliary non-head-worn unit carrying the processing circuitry.

The non-invasive product customization system further comprises at least one processor configured for determining a mental state (e.g., one of an emotional state, a cognitive state, and a perceptive state) of the user based on the detected brain activity, and modifying the product formulation within a virtual mixing container (e.g., by adding a selected ingredient to the product formulation within the virtual mixing container, discarding a selected ingredient from the product formulation within the virtual mixing container, and/or modifying a dosage of a selected existing ingredient in the product formulation within the virtual mixing container) based on the determined mental state of the user.

In one embodiment, the processor(s) is configured for determining a level of the mental state (e.g., one of an emotional state, a cognitive state, and a perceptive state) of the user based on the detected brain activity, and modifying the product formulation based on the level of the determined mental state of the user. The processor(s) may be configured for being manually programmed with the determined mental state. The non-invasive product customization system may optionally comprise a sensory input device configured for presenting the product formulation to the user for input into the brain of the user via the sensory nervous system of the user. The processor(s) may be further configured for combining ingredients of the modified product formulation into a final product formulation. In one embodiment, a portion of the processor(s) is contained in the brain interface assembly for determining the mental state of the user based on the detected brain activity, and another portion of the processor(s) is contained in a peripheral device for modifying the product formulation within the virtual mixing container based on the determined mental state of the user.

In accordance with a second aspect of the present inventions, a method of customizing a product formulation comprises detecting brain activity of a user (e.g., while the user is in a normal life and work environment) in response to an input of a product formulation (e.g., one or more of a fragrance, homeopathic oil for external therapeutic applications, lotion, food, drink, and psychotropic substances) into a brain of the user via a sensory nervous system (e.g., olfactory sensory system and/or gustatory sensory system) of the user. In one method, the brain activity is optically detected. In another method, the brain activity is magnetically detected. The brain activity of the user may be detected, e.g., by detecting energy from a brain of the user, and identifying the brain activity in response to detecting the energy from the brain of the user.

The method further comprises determining a mental state (e.g., one of an emotional state, a cognitive state, and a perceptive state) of the user based on the detected brain activity, and modifying the product formulation (e.g., by adding a selected ingredient to the product formulation, discarding a selected ingredient from the product formulation, and/or modifying a dosage of a selected existing ingredient in the product formulation) based on the determined mental state of the user. In one method, determining the mental state of the user based on the detected brain activity comprises determining a level of the mental state of the user based on the detected brain activity, in which case, the product formulation may be modified based on the level of the determined mental state of the user. Another method further comprises combining ingredients of the modified product formulation into a final product formulation.

In accordance with a third aspect of the present inventions, a non-invasive mental state modulation system comprises a sensory input device configured for presenting a product formulation (e.g., one or more of a fragrance, homeopathic oil for external therapeutic applications, lotion, food, drink, and psychotropic substances) into a brain of the user via a sensory nervous system (e.g., olfactory sensory system and/or gustatory sensory system) of the user.

The non-invasive mental state modulation system further comprises a non-invasive brain interface assembly configured for detecting brain activity of the user (e.g., while the user is in a normal life and work environment). In one embodiment, the non-invasive brain interface assembly is an optical measurement assembly. In another embodiment, the non-invasive brain interface assembly is a magnetic measurement assembly. The non-invasive brain interface assembly may comprise, e.g., at least one detector configured for detecting energy from a brain of the user, and processing circuitry configured for identifying the brain activity in response to detecting the energy from the brain of the user. The non-invasive brain interface assembly may comprise a head-worn unit carrying the at least one detector, and an auxiliary non-head-worn unit carrying the processing circuitry.

The non-invasive mental state modulation system further comprises at least one processor configured for determining a mental state of the user based on the detected brain activity, and in response to the determined mental state of the user, for automatically instructing the sensory input device to present the product formulation to the user in a manner that modulates the mental state of the user. Preferably, the product formulation is presented to the user in a manner that promotes a positive mental state (e.g., one of joy, relaxation, and a cognitive state) of the user.

In one embodiment, the determined mental state of the user is a negative mental state (e.g., one of anxiety and fear), and the mental state of the user is modulated to promote a positive mental state (e.g., one of joy, relaxation, and a cognitive state) of the user. In another embodiment, the processor(s) is further configured for being manually programmed with the positive mental state. In still another embodiment, a portion of the processor(s) is contained in the brain interface assembly for determining the mental state of the user based on the detected brain activity, and another portion of the processor(s) is contained in a peripheral device for modifying the product formulation within the virtual mixing container based on the determined mental state of the user.

In accordance with a fourth aspect of the present inventions, a method of modulating a mental state (e.g., one of an emotional state, a cognitive state, and a perceptive state) of a user comprises detecting brain activity of the user (e.g., while the user is in a normal life and work environment). In one method, the brain activity is optically detected. In another method, the brain activity is magnetically detected. The brain activity of the user may be detected, e.g., by detecting energy from a brain of the user, and identifying the brain activity in response to detecting the energy from the brain of the user.

The method further comprises determining a mental state (e.g., one of an emotional state, a cognitive state, and a perceptive state) of the user based on the detected brain activity, and automatically presenting the product formulation (e.g., one or more of a fragrance, homeopathic oil for external therapeutic applications, lotion, food, drink, and psychotropic substances) into a brain of the user via a sensory nervous system (e.g., olfactory sensory system and/or gustatory sensory system) of the user in a manner that modulates the mental state of the user. In one method, the determined mental state of the user is a negative mental state (e.g., one of anxiety and fear), and the mental state of the user is modulated to promote a positive mental state (e.g., one of joy, relaxation, and a cognitive state) of the user.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which:

FIGS. 2A-2E are diagrams illustrating the modification of ingredients within the mixing container by the non-invasive product formulization system of FIG. 1;

DETAILED DESCRIPTION OF THE EMBODIMENTS

Figure 1:
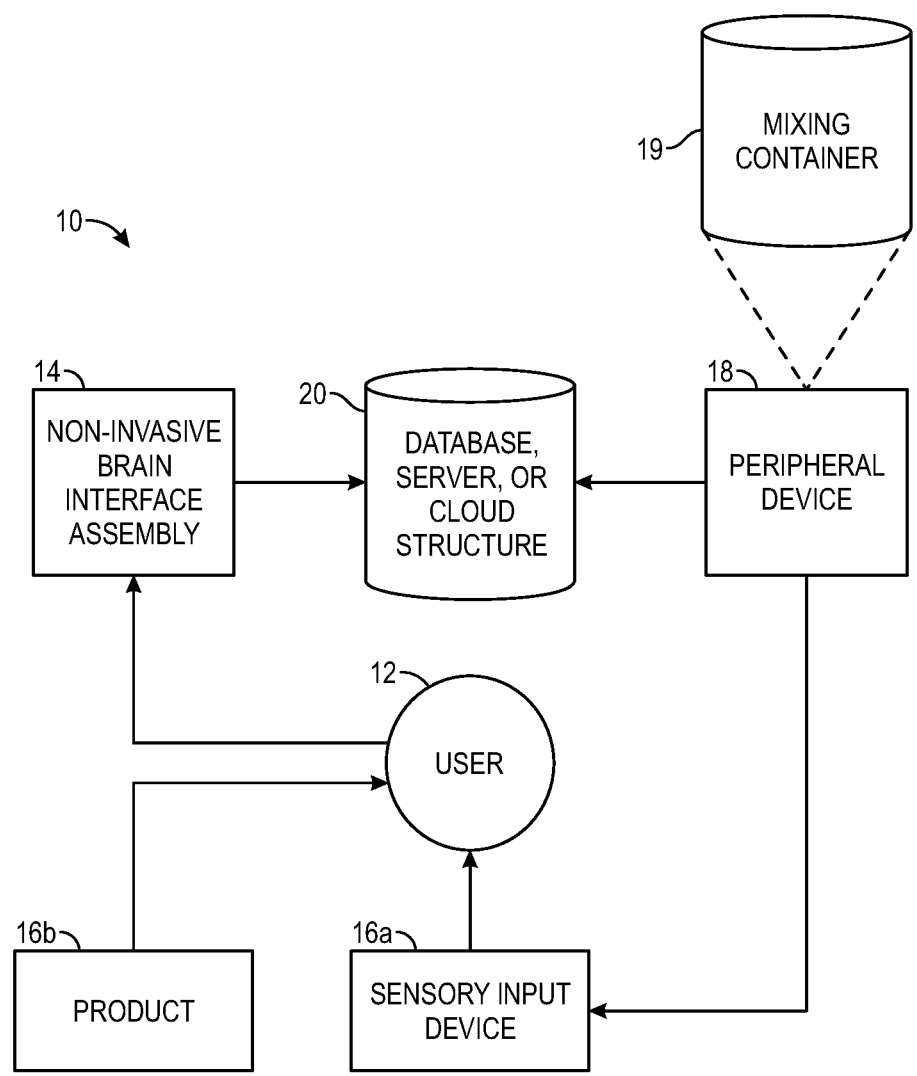
FIG. 1 is a block diagram of a non-invasive product formulization system constructed in accordance with one embodiment of the present inventions.

Referring now to FIG. 1, a generalized embodiment of a non-invasive product customization system 10 constructed in accordance with the present inventions will be described. As will be described in further detail below, the non-invasive product customization system 10 facilitates the customization of the formulation of a product; e.g., a fragrance, homeopathic oil for external therapeutic applications, lotion, food, drink (e.g., a coffee drink with customized blend of selected coffee beans, caffeine content, and flavor such as vanilla), psychotropic substances, and the like, to a user 12 (or alternatively, a group of people in the same class as the user 12) without requiring voluntary sensory feedback from the user 12. As will be also described in further detail below, the non-invasive product formulization system may optionally serve as a non-invasive mental state modulation system that presents product formulations to the user 12 in order to modulate a mental state of the user 12, e.g., a negative mental state to a positive mental state.

To this end, the non-invasive product system 10 comprises a non-invasive brain interface assembly 14 configured for detecting brain activity of the user 12. As will be discussed in further detail below, the brain interface assembly 14 can be optically-based, magnetically-based, or based on any other modality that enables it to non-invasively detect brain activity of the user 12 (i.e., through the intact skin and skull of the user 12), through the use of sensitive electronics, as will be described below, and is designed to be worn by the user 12. As will also be discussed in further detail below, the non-invasive brain interface assembly 14 is portable in that it can be worn by the user 12. In this manner, the non-invasive product customization system 10 may be conveniently used in a normal life and working environment. For the purposes of this specification, a "normal life and work environment" is an environment that is usual and ordinary, and thus, necessitates that the user 12 be able to freely ambulate without any physical hindrance by the system 10 or other system to which the system 10 is coupled or otherwise is an adjunct. Thus, a normal life and work environment excludes a clinical setting (e.g., any setting in which a conventional magnetic resonance imaging (MRI) machine or computed tomography (CT) could potentially be used to detect neural activity from the user). In alternative embodiments, the non-invasive brain interface assembly 16 may be non-portable and/or non-wearable in cases where it is suitable for the non-invasive brain interface assembly 14 to be operated outside of a normal life and working environment, e.g., in a food research facility or laboratory.

The brain interface assembly 14 is configured for determining a mental state based on the detected brain activity of the user 12, although this function can be performed by other processing components in the non-invasive product customization system 10, as described in further detail below. The mental state of the user 12 may include, e.g., an emotional state (e.g., joy, excitement, relaxation, surprise, anxiety, sadness, anger, disgust, contempt, fear, etc.), a cognitive state encompassing intellectual functions and processes (e.g., memory retrieval, focus, attention, creativity, reasoning, problem solving, decision making, comprehension and production of language, etc.), or a perceptive state (e.g., face perception, color perception, sound perception, visual perception, etc.).

The mental state of the user 12 may be determined based on the detected brain activity in any one of a variety of manners. In one embodiment, a univariate approach in determining the mental state of the user 12 may be performed, i.e., the brain activity can be detected in a plurality (e.g., thousands) of separable cortical modules of the user 12, and the brain activity obtained from each cortical module can be analyzed separately and independently. In another embodiment, a multivariate approach in determining the mental state of the user 12 may be performed, i.e., the brain activity can be detected in a plurality (e.g., thousands) of separable cortical modules of the user 12, and the full spatial pattern of the brain activity obtained from the cortical modules can be assessed together.

Any one of a variety of models can be used to classify the mental state of the user 12, and will highly depend on the characteristics of brain activity that are input onto the models. Such characteristics of brain activity may typically be extracted from the spatiotemporal brain activity that is captured, and can include, e.g., location of signal, fine grained pattern within or across locations, amplitude of signal, timing of response to behavior, magnitude of frequency bands of the signal (taking the Fourier transform of the time series), ratio of magnitude of frequency bands, cross-correlation between time series of signal between two or more locations captured simultaneously, spectral coherence between two or more locations captured simultaneously, components that maximize variance, components that maximize non-gaussian similarity, etc. The characteristics of brain activity selected to be input into the models must be considered in reference to univariate and multivariate approaches, since the univariate approach, e.g., focuses on a single location, and therefore will not take advantage of features that correlate multiple locations. The characteristics of the brain activity can be extracted from preprocessed raw data recorded during situations of patterns of thought and perception in everyday life, which are characterized by a continually changing stream of consciousness. The preprocessing of the raw data typically involves filtering the data (either in the time domain or the frequency domain) to smooth, remove noise, and separate different components of signal.

Selecting a model will be heavily dependent on whether the data is labeled or unlabeled (meaning is it known what the user is doing at the time that the brain activity is detected), as well as many other factors (e.g., is the data assumed to be normally distributed, is the data assumed relationship linear, is the data assumed relationship non-linear, etc.) Models can include, e.g., support vector machines, expectation maximization techniques, naïve-Bayesian techniques, neural networks, simple statistics (e.g., correlations), deep learning models, pattern classifiers, etc.

These models are typically initialized with some training data (meaning that a calibration routine can be performed on the user to determine what the user is doing). If no training information can be acquired, such models can be heuristically initialized based on prior knowledge, and the models can be iteratively optimized with the expectation that optimization will settle to some optimal maximum or minimum solution. Once it is known what the user is doing, the proper characteristics of the neural activity and proper models can be queried. The models may be layered or staged, so that, e.g., a first model focuses on pre-processing data (e.g., filtering), the next model focuses on clustering the preprocessed data to separate certain features that may be recognized to correlate with a known activity performed by the user, and then the next model can query a separate model to determine the mental state based on that user activity.

As will be described in further detail below, the training data or prior knowledge of the user may be obtained by providing known life/work context to the user. Altogether, the models can be used to track mental state and perception under natural or quasi-natural (i.e., in response to providing known life/work context to the user) and dynamic conditions taking in the time-course of averaged activity and determining the mental state of the user based on constant or spontaneous fluctuations in the characteristics of the brain activity extracted from the data.

A set of data models that have already been proven, for example in a laboratory setting, can be initially uploaded to the non-invasive product customization system 10, which system will then use the uploaded models to determine the mental state of the user. Optionally, the non-invasive product customization system 10 may collect data during actual use with the user, which can then be downloaded and analyzed in a separate server, for example in a laboratory setting, to create new or updated models. Software upgrades, which may include the new or updated models, can be uploaded to the non-invasive product customization system 10 to provide new or updated data modelling and data collection.

Further details regarding determining the mental state of a person based on detected brain activity can be found in a variety of peer-reviewed publications. See, e.g., Lee, B. T., Seok, J. H., Lee., B. C, Cho, S. W., Chai, J. H., Choi, I. G., Ham, B. J., "Neural correlates of affective processing in response to sad and angry facial stimuli in patients with major depressive disorder," *Prog Neuropsychopharmacol Biol Psychiatry,* 32(3), 778-85 (2008); A. C. Felix-Ortiz, A. C., Burgos-Robles, A., Bhagat, N. D., Leppla, C. A., Tye, K. M."Bidirectional modulation of anxiety-related and social behaviors by amygdala projections to the medial prefrontal cortex," *Neuroscience* 321, 197-209 (2016); Beauregard, M., Levesque, J. & Bourgouin, P., "Neural correlates of conscious self-regulation of emotion," *J. Neurosci.* (2001): 21, RC165; Phan, K. L., Wager, T., Taylor, S. F. & Liberzon, I., "Functional neuroanatomy of emotion: a meta-analysis of emotion activation studies in PET and fMRI," *Neuroimage,* 16, 331-348 (2002); Canli, T. & Amin, Z., "Neuroimaging of emotion and personality: scientific evidence and ethical considerations," *Brain Cogn.,* 50, 414-431 (2002), McCloskey, M. S., Phan, K. L. & Coccaro, E. F., "Neuroimaging and personality disorders," *Curr. Psychiatry Rep.,* 7, 65-72 (2005); Heekeren, H. R., Marrett, S., Bandettini, P. A. & Ungerleider, L. G., "A general mechanism for perceptual decision-making in the human brain," *Nature,* 431, 859-862 (2004); Shin L M, Rauch S L, Pitman R K. Amygdala, Medial Prefrontal Cortex, and Hippocampal Function in PTSD, *Ann N Y Acad Sci.,* 1071(1) (2006); Lis E, Greenfield B, Henry M, Guile J M, Dougherty G., "Neuroimaging and genetics of borderline personality disorder: a review," *J Psychiatry Neurosci.,* 32(3), 162-173 (2007); Etkin A, Wager T D, "Functional neuroimaging of anxiety: a meta-analysis of emotional processing in PTSD, social anxiety disorder, and specific phobia," Am J Psychiatry, 164(10), 1476-1488 (2007); Etkin A. Functional Neuroimaging of Major Depressive Disorder: A Meta-Analysis and New Integration of Baseline Activation and Neural Response Data, *Am J Psychiatry,* 169(7), 693-703 (2012); Sheline Y I, Price J L, Yan Z, Mintun M A, "Resting-state functional MRI in depression unmasks increased connectivity between networks via the dorsal nexus, *Proc Natl Acad Sci.,* 107(24), 11020-11025 (2010); Bari A, Robbins T W, "Inhibition and impulsivity: Behavioral and neural basis of response control," *Prog Neurobiol.,* 108:44-79 (2013); Kagias, Konstantinos et al. "Neuronal responses to physiological stress," Frontiers in genetics, 3:222 (2012).

The non-invasive product customization system 10 further comprises a sensory input device 16a or a product 16b (collectively, a sensory input/product 16) configured for providing different product formulation inputs into the brain of the user 12 via the sensory nervous system of the user 12. For example, the different product formulations can be inhaled and/or ingested by the user 12, in which case, the sensory envious system through which the different product formulations are input into the brain of the user 12 may be the olfactory sensory system and/or the gustatory sensory system. The sensory input device 16a may comprise, e.g., a mask or tube that conveys different product formulations to the vicinity of the nose of the user 12. Alternatively, the different product formulations can be presented to the user 12 in the form of the actual product 16b, itself. That is, the user 12 may simply smell or taste the product. The different product formulations may include different ingredients or different doses of the same ingredient. For example, a first product formulation may include ingredient A, ingredient B, and ingredient C; and a second product formulation may include ingredient A, ingredient C, ingredient D, and ingredient E. Or, a first product formulation may include a first dose of ingredient A, and a first dose of ingredient B, and a second product formulation may include a second different dose of ingredient A and a second different dose (or the same first dose) of ingredient B. Examples of product formulations 200 are shown in FIGS. 2A-2E and described below.

The non-invasive product customization system 10 further comprises a peripheral device 18 (e.g., a Smartphone, tablet computer, or the like) configured for programming a desired mental state or mental states of the user 12 to be monitored by the brain interface assembly 14 in relation to the product formulation that is to be tested. Such mental state(s) of the user 12 can be individually programmed using a manual selection or manual input on the peripheral device 18 by the user 12, and can be made available through the graphical user interface of the peripheral device 18 though a button, tab, or icon, e.g., through the use of a radio button or similar selectable options, representing one of a set of options of individual experiences.

The peripheral device 18 is also configured for modifying the product formulation using a virtual mixing container 19 based on the determined mental state of the user 12. As examples, the peripheral device 18 may be configured for modifying the product formulation by adding a selected ingredient to the product formulation within the virtual mixing container 19, discarding a selected ingredient from the product formulation within virtual mixing container 19, and/or modifying a dosage of a selected existing ingredient in the product formulation within the virtual mixing container 19. Although the virtual mixing container 19 is shown as being incorporated into the peripheral device 18, the virtual mixing container 19 may be incorporated into a separate device.

Preferably, the peripheral device 18 is ultimately configured for determining the optimized product formulation that best promotes the desired mental state(s) programmed into the peripheral device 18. This can be accomplished by, e.g., by repeatedly detecting additional brain activity of the user 12 via the brain interface assembly 14 in response to inputs of differently modified product formulations into the brain of the user via the sensory nervous system of the user 12, and repeatedly determining the modified mental states of the user 12 based on the additionally detected brain activity of the user 12 via the peripheral device 18. Once the product formulation has been optimized, the peripheral device 18 may be configured for combining the ingredients of the optimized product formulation into a final product formulation. The peripheral device 18 may also be further configured for repeatedly validating the optimized product formulation to ensure that the product formulation within the mixing container 19, continues to promote the desired mental state(s) of the user 12.

The peripheral device 18 may also be configured for associating each final product formulation to a particular programmed mental state, such that the peripheral device 18 may instruct the sensory input device 16a to present a particular product formulation to the user 12 in a manner that modulates the mental state of the user 12 to the programmed mental state. For example, if the peripheral device 18 determines that the user 12 has a negative mental state (e.g., anxiety or fear), the peripheral device 18 may be configured for automatically selecting one of the final product formulations corresponding to a positive mental state (e.g., joy, relaxation, or a cognitive state), and instructing the sensory input device 16a to present the selected product formulation to the user 12 in a manner that modulates the mental state of the user 12 to the positive mental state.

The non-invasive product customization system 10 also optionally comprises a database, server, or cloud structure 20 configured for tracking the brain activity of the user 12. For example, the database, server, or cloud structure 20 may be configured to collect raw data (e.g., brain activity data) generated by the brain interface assembly 14. Furthermore, the database, server, or cloud structure 20 (independently of or in conjunction with the mental state determination functions of the brain interface assembly 14) may be configured for performing a data analysis of the raw data in order to determine the mental state of the user 12.

For example, if the raw data obtained by the user 12 is being anonymized and stored in the database, server, or cloud structure 20, the data models can be pooled across various users, which deep learning algorithms would benefit from. The database, server, or cloud structure 20 may be configured for performing cross-correlation analysis of the signal data analysis in order to reduce the pool size of the database and focus subject averaged data to a pool that is similar to the user. Most likely, each user will have a portion of their model optimized to them, but then another portion takes advantage of patterns extracted from a larger pool of users. It should also be appreciated that each user may perform any variety of an infinite number of activities. Thus, even if a user is properly calibrated, such calibration will only be for a small set of infinite possibilities. Generalizing models may comprise various variabilities and optimizing may be difficult. However, by building a large user database on the database, server, or cloud structure 20, a data analysis pipeline connected to such database, server, or cloud structure 20 can preprocess data (clean it up), extract all different kinds of features, and then apply an appropriate data model, to overcome this issue. The brain activity of the user 12 may be tracked with additional life/work context to acquire meta data in depth assessment of awareness and behavior modulation patterns of the user 12. Although, all of the tracked data analysis has been described as being performed by the database, server, or cloud structure 20, it should be appreciated that at least a portion of the tracked data analysis functionality may be incorporated in the peripheral device 18, with the caveat that it is preferred that the tracking of the brain activity between a pool of users be performed by the database, server, or cloud structure 20.

Figure 3:
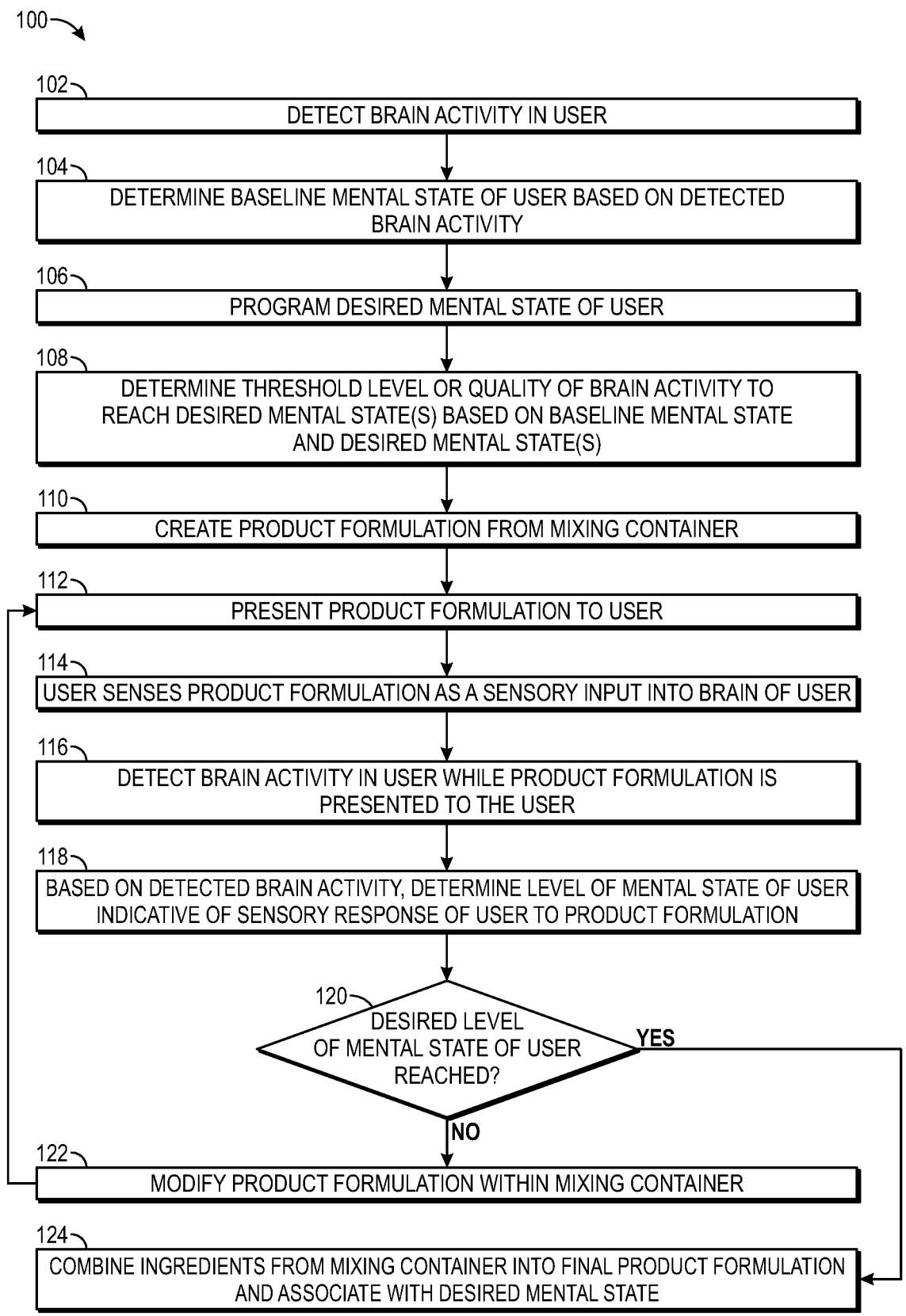
FIG. 3 is a flow diagram illustrating one method of operating the non-invasive product formulization system of FIG. 1.

Having described the structure, function, and application of data models of the non-invasive product customization system 10, one method 100 of operating the non-invasive product customization system 10 will now be described with reference to FIG. 3.

Initially, the brain interface assembly 14 detects the brain activity of the user 12 (step 102). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the peripheral device 18 or database, server, or cloud structure 20) then determines a baseline mental state of the user 12 based on the detected brain activity (step 104). The user 12 then programs the peripheral device 18 with the desired mental state or mental states (e.g., joy) (step 106). The peripheral device 18 then performs an analysis of the baseline mental state of the user 12 and the desired mental state(s) of the user 12 (step 108). In this manner, the brain interface assembly 14 can be calibrated to the desired mental state(s) of the user 12, such that a threshold level or quality of the brain activity of the user 12 corresponding to the desired mental state(s) can be determined. Thus, the user 12 will be determined to have reached the mental state(s) only after the detected brain activity of the user 12 has exceeded the threshold level or quality.

The peripheral device 18 then optimizes the product formulation by presenting different product formulations to the user 12 via the sensory input device/product 16. In particular, the peripheral device 18 creates a product formulation from the virtual mixing container 19 (examples of product formulations are shown in FIGS. 2A-2D) (step 110) and presents the product formulation to the user 12 via the sensory input device/product 16 (step 112). The user 12 senses the product formulation, e.g., via smell and/or taste, and is input through the sensory nervous system to the brain of the user 12 (step 114). As such, the sensory input device/product 16 serves as brain input to the user 12 through the sensory nervous system.

Next, the brain interface assembly 14 detects the brain activity of the user 12 while the sensory input device/product 16 presents the product formulation to the user 12 (step 116), and then the brain interface assembly 14 (or alternatively, the peripheral device 18 or database, server, or cloud structure 20), based on the detected brain activity, determines a level of the mental state of the user 12 indicative of the sensory response of the user 12 to the presented product formulation (step 118).

If the level of the desired mental state(s) of the user 12 has not been reached (step 120), the peripheral device 18 modifies the product formulation within the mixing container 19 to arrive at a new product formulation (step 122), and then returns to step 112 where the peripheral device 18 presents the product formulation to the user 12 via the sensory input device/product 16, and steps 114-120 are repeated as required until the level of the desired mental state of the user 12 is reached in response to the new product formulation. For example, as illustrated in FIG. 2A, the mixing container 19 may currently contain various ingredients, in this example, 7 ingredients are shown. The peripheral device 18 may change one selected ingredient at time, e.g., by retaining the selected ingredient, but changing the dosage of the selected ingredient in the mixing container 19. For example, as illustrated in FIG. 2B, the dosage of selected ingredient 3 has been increased, and as illustrated in FIG. 2C, the dosage of selected ingredient 3 has been decreased. In other examples, selected ingredient 3 has been discarded from the mixing container 19, as illustrated in FIG. 2D, and new ingredient 8 has been added to the mixing container 19, as illustrated in FIG. 2E.

If the level of the desired mental state of the user 12 has been reached (step 120), the peripheral device 18 combines all of the ingredients from the mixing container 19 into the final product formulation that is associated with the desired mental state (step 124). This final product formulation can be used by the user 12 or a group of people in the same class as the user 12. The peripheral device 18 may periodically validate the final product formulation by returning to step 112, and modifying the product formulation to ensure that the product formulation evokes the level of the desired mental state(s) in the use 12, and optionally to improve the mental state of the user 12.

Figure 4:
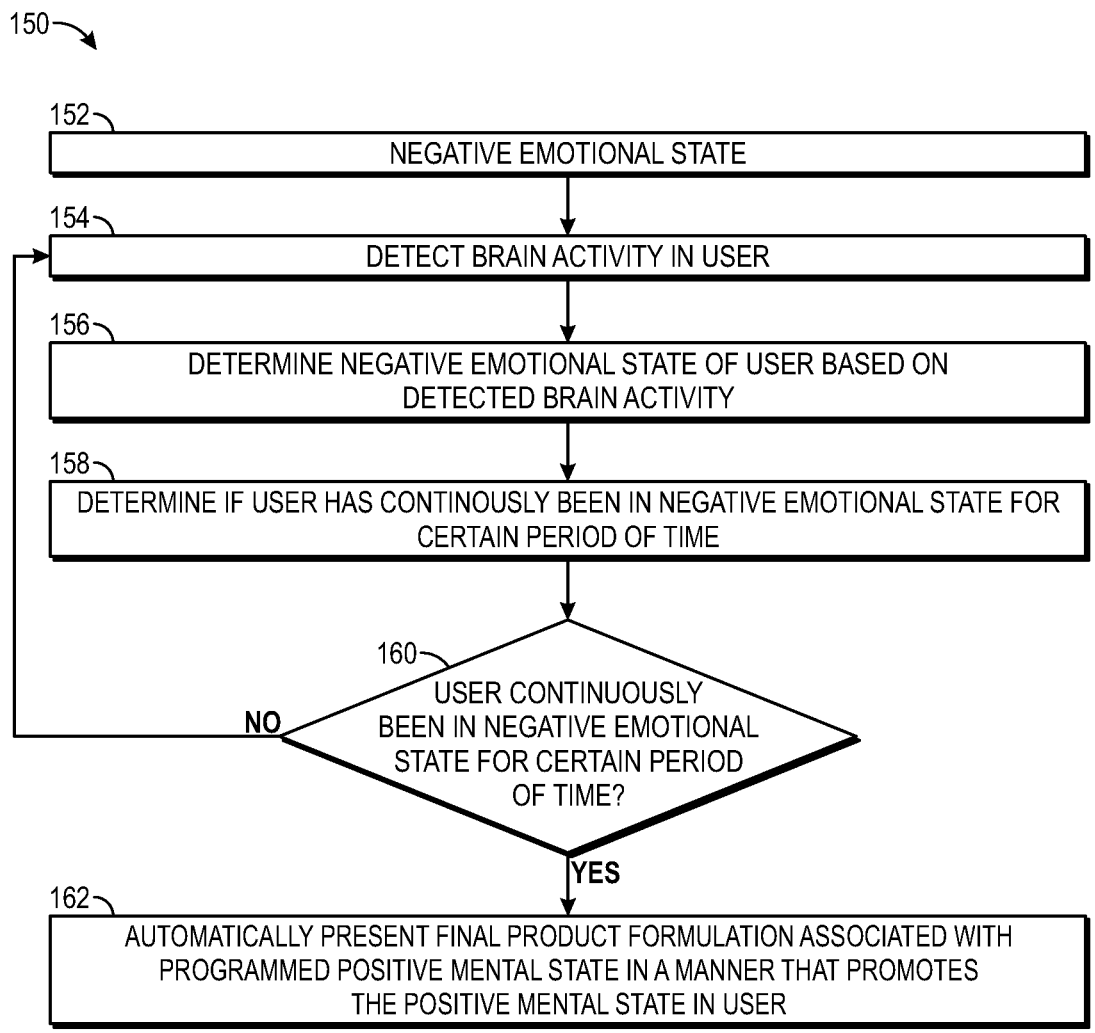
FIG. 4 is a flow diagram illustrating one method of operating the non-invasive product formulization system of FIG. 1 as a non-invasive mental state modulation system.

As briefly discussed above, the non-invasive product customization system 10 may optionally serve as a non-invasive mental statement modulation system that presents product formulations to the user 12 in order to modulate a mental state of the user 12. One method 150 of operating the non-invasive mental statement modulation system will now be described with reference to FIG. 4.

Initially, the user 12 may initially have a mental state, which may be conscious or subconscious (step 152). In the illustrated method, the initial mental state is a negative emotional state (e.g., anxiety or fear), although other negative mental states are contemplated, as set forth above. The brain interface assembly 14 detects the brain activity of the user 12 (step 154). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the database, server, or cloud structure 20) then determines that the user 12 has a negative emotional state based on the detected brain activity (step 156).

Next, the peripheral device 18 determines whether the user 12 has been continually in the negative emotional state for a certain period of time, e.g., one, two, five, ten minutes, etc., which period of time may be preprogrammed (step 158). If the user 12 is determined to be continually in the negative emotional state for the certain period of time (step 160), the peripheral device 18 automatically instructs the sensory input device 16 to present the final product formulation associated with the programmed mental state (preferably, a positive mental state, e.g., joy, relaxation, or a cognitive state), thereby promoting the programmed mental state (step 162), although the promotion of other positive mental states is also contemplated as set forth above. If the user 12 is determined to not be continually in the determined negative emotional state for the certain period of time (step 160), the peripheral device 16 does not automatically instruct the sensory input device 16 to present the final product formulation associated with the programmed mental state, but rather returns to step 154.

Figure 5:
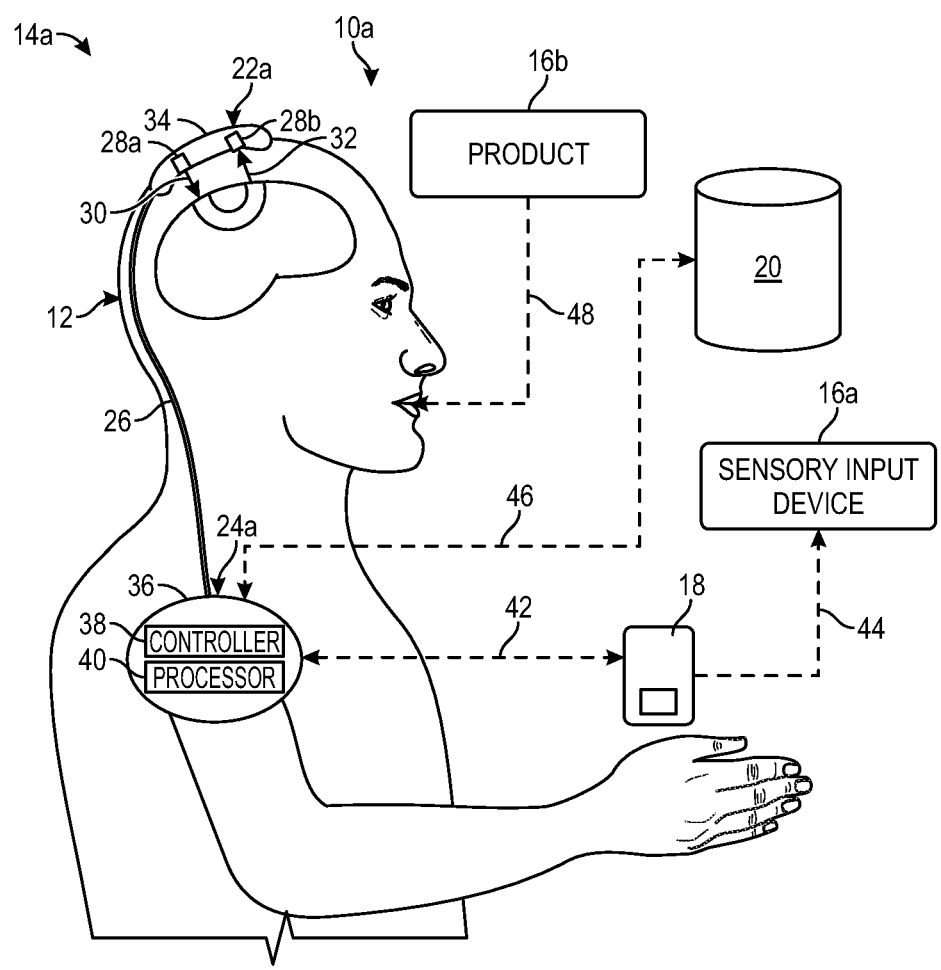
FIG. 5 is a view of one specific physical embodiment of the non-invasive product formulization system of FIG. 1.

Referring to FIG. 5, a physical implementation of one embodiment of a non-invasive product customization system 10a will now be described. The non-invasive product customization system 10a comprises an optically-based non-invasive brain interface assembly 14a, which may, e.g., incorporate any one or more of the neural activity detection technologies described in U.S. patent application Ser. No. 15/844,370, entitled "Pulsed Ultrasound Modulated Optical Tomography Using Lock-In Camera" (now U.S. Pat. No. 10,335,036), U.S. patent application Ser. No. 15/844,398, entitled "Pulsed Ultrasound Modulated Optical Tomography With Increased Optical/Ultrasound Pulse Ratio" (now U.S. Pat. No. 10,299,682), U.S. patent application Ser. No. 15/844,411, entitled "Optical Detection System For Determining Neural Activity in Brain Based on Water Concentration" (now U.S. Pat. No. 10,420,469), U.S. patent application Ser. No. 15/853,209, entitled "System and Method For Simultaneously Detecting Phase Modulated Optical Signals" (now U.S. Pat. No. 10,016,137), U.S. patent application Ser. No. 15/853,538, entitled "Systems and Methods For Quasi-Ballistic Photon Optical Coherence Tomography In Diffusive Scattering Media Using a Lock-In Camera" (now U.S. Pat. No. 10,219,700), U.S. patent application Ser. No. 16/266,818, entitled "Ultrasound Modulating Optical Tomography Using Reduced Laser Pulse Duration," U.S. patent application Ser. No. 16/299,067, entitled "Non-Invasive Optical Detection Systems and Methods in Highly Scattering Medium," U.S. patent application Ser. No. 16/379,090, entitled "Non-Invasive Frequency Domain Optical Spectroscopy For Neural Decoding," U.S. patent application Ser. No. 16/382,461, entitled "Non-Invasive Optical Detection System and Method," U.S. patent application Ser. No. 16/392,963, entitled "Interferometric Frequency-Swept Source And Detector In A Photonic Integrated Circuit," U.S. patent application Ser. No. 16/392,973, entitled "Non-Invasive Measurement System and Method Using Single-Shot Spectral-Domain Interferometric Near-Infrared Spectroscopy Based On Orthogonal Dispersion, U.S. patent application Ser. No. 16/393,002, entitled "Non-Invasive Optical Detection System and Method Of Multiple-Scattered Light With Swept Source Illumination," U.S. patent application Ser. No. 16/385,265, entitled "Non-Invasive Optical Measurement System and Method for Neural Decoding," U.S. patent application Ser. No. 16/533,133, entitled "Time-Of-Flight Optical Measurement And Decoding Of Fast-Optical Signals," U.S. patent application Ser. No. 16/565,326, entitled "Detection Of Fast-Neural Signal Using Depth-Resolved Spectroscopy," U.S. patent application Ser. No. 16/226,625, entitled "Spatial and Temporal-Based Diffusive Correlation Spectroscopy Systems and Methods," U.S. Provisional Patent Application Ser. No. 62/772,584, entitled "Diffuse Correlation Spectroscopy Measurement Systems and Methods," U.S. patent application Ser. No. 16/432,793, entitled "Non-Invasive Measurement Systems with Single-Photon Counting Camera," U.S. Provisional Patent Application Ser. No. 62/855,360, entitled "Interferometric Parallel Detection Using Digital Rectification and Integration", U.S. Provisional Patent Application Ser. No. 62/855,380, entitled "Interferometric Parallel Detection Using Analog Data Compression," U.S. Provisional Patent Application Ser. No. 62/855,405, entitled "Partially Balanced Interferometric Parallel Detection," which are all expressly incorporated herein by reference.

The brain interface assembly 14a includes a wearable unit 22a configured for being applied to the user 12, and in this case, worn on the head of the user 12; and an auxiliary head-worn or non-head-worn unit 24a (e.g., worn on the neck, shoulders, chest, or arm). Alternatively, the functionality of the unit 24a may be incorporated into the head-worn unit 22a. The auxiliary non-head-worn unit 24a may be coupled to the head-worn unit 22a via a wired connection 26 (e.g., electrical wires). Alternatively, the brain interface assembly 14a may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22a and the auxiliary unit 24a.

The head-worn unit 22a comprises electronic or optical components, such as, e.g., one or more optical sources, an interferometer, one or more optical detector(s) (not shown), etc., an output port 28a for emitting sample light 30 generated by the brain interface assembly 14a into the head of the user 12, an input port 28b configured for receiving neural-encoded signal light 32 from the head of the user 12, which signal light is then detected, modulated and/or processed to determine brain activity of the user 12, and a support housing structure 34 containing the electronic or optical components, and ports 28a, 28b.

The support housing structure 34 may be shaped, e.g., have a banana, headband, cap, helmet, beanie, other hat shape, or other shape adjustable and conformable to the user's head, such that the ports 28a, 28b are in close contact with the outer skin of the head, and in this case, the scalp of the user 12. The support housing structure 34 may be made out of any suitable cloth, soft polymer, plastic, hard shell, and/or any other suitable material as may serve a particular implementation. In an alternative embodiment, optical fibers (not shown) may be respectively extended from the ports 28a, 28b, thereby freeing up the requirement that the ports 28a, 28b be disposed in close proximity to the surface of the head. In any event, an index matching fluid may be used to reduce reflection of the light generated by the head-worn unit 22a from the outer skin of the scalp. An adhesive, strap, or belt (not shown) can be used to secure the support housing structure 34 to the head of the user 12.

The auxiliary unit 24a comprises a housing 36 containing a controller 38 and a processor 40. The controller 38 is configured for controlling the operational functions of the head-worn unit 22a, whereas the processor 40 is configured for processing the neural-encoded signal light 32 acquired by the head-worn unit 22a to detect and localize the brain activity of the user 12, as well as to determine the mental state of the user 12 based on the brain activity of the user 12 if not performed by other processing units in the system 10a. The auxiliary unit 24a may additionally include a power supply (which if head-worn, may take the form of a rechargeable or non-chargeable battery), a control panel with input/output functions, a display, and memory. Alternatively, power may be provided to the auxiliary unit 24a wirelessly (e.g., by induction).

The functionalities of the sensory input device/product 16, peripheral device 18 (along with the mixing container 19 (shown in FIG. 1), and database, server, or cloud structure 20 may be the same as described above with respect to the non-invasive product customization system 10 of FIG. 1.

The peripheral device 18 is coupled to the auxiliary unit 24a of the brain interface assembly 14a via a wireless connection 42 (e.g., wireless radio frequency (RF) signals (e.g., Bluetooth, Wifi, cellular, etc.) or optical links (e.g., fiber optic or infrared (IR)) for communicating between the peripheral device 18 and the brain interface assembly 14a. The peripheral device 18 is also coupled to the sensory input device 16a via a wireless connection 44 (e.g., wireless radio frequency (RF) signals (e.g., Bluetooth, Wifi, cellular, etc.) or optical links (e.g., fiber optic or infrared (IR)) for communicating between the peripheral device 18 and the sensory input device 16a. Alternatively, wired connections between the peripheral device 18 and the brain interface assembly 14a and/or the sensory input device 16a may be used. Alternatively or optionally, the product 16b may simply be in the vicinity of the user 12 to provide a natural path 48 in the ambient environment through which the user 12 may sense the product 16b.

The database, server, or cloud structure 20 may be coupled to the auxiliary unit 24a of the brain interface assembly 14a (and/or the peripheral device 18) via a wireless connection 46 (e.g., wireless radio frequency (RF) signals (e.g., Bluetooth, Wifi, cellular, etc.) or optical links (e.g., fiber optic or infrared (IR)) for communicating between the database, server, or cloud structure 20 and the brain interface assembly 14a and peripheral device 18. Alternatively, a wired connection between the database, server, or cloud structure 20 and the auxiliary unit 24a of the brain interface assembly 14a and/or the peripheral device 18 may be used.

Figure 6:
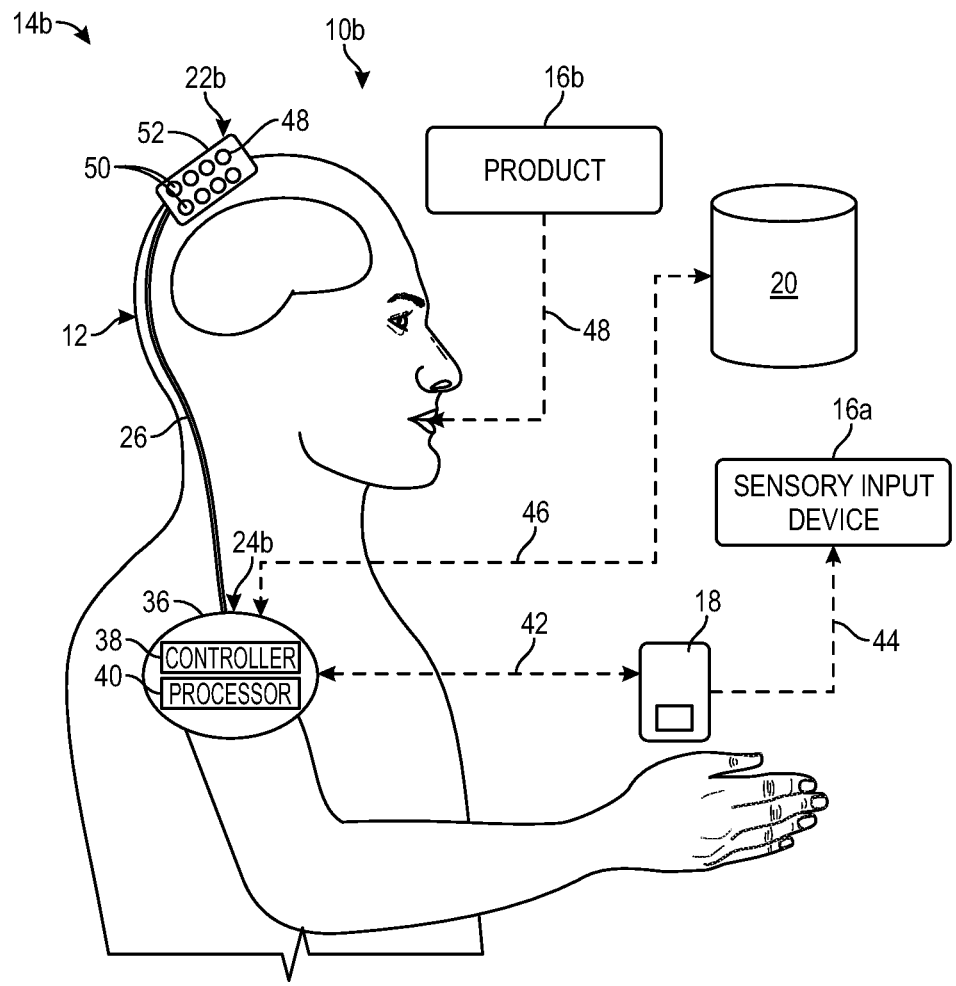
FIG. 6 is a view of another specific physical embodiment of the non-invasive product formulization system of FIG. 1.

Referring to FIG. 6, a physical implementation of one embodiment of a non-invasive product customization system 10b will now be described. The system 10b comprises an optically-based, time-domain, non-invasive brain interface assembly 14b, which may, e.g., incorporate any one or more of the neural activity detection technologies described in U.S. Non-Provisional patent application Ser. No. 16/051,462, entitled "Fast-Gated Photodetector Architecture Comprising Dual Voltage Sources with a Switch Configuration" (now U.S. Pat. No. 10,158,038), U.S. patent application Ser. No. 16/202,771, entitled "Non-Invasive Wearable Brain Interface Systems Including a Headgear and a Plurality of Self-Contained Photodetector Units Configured to Removably Attach to the Headgear" (now U.S. Pat. No. 10,340,408), U.S. patent application Ser. No. 16/283,730, entitled "Stacked Photodetector Assemblies" (now U.S. Pat. No. 10,515,993), U.S. patent application Ser. No. 16/544,850, entitled "Wearable Systems with Stacked Photodetector Assemblies," U.S. Provisional Patent Application Ser. No. 62/880,025, entitled "Photodetector Architectures for Time-Correlated Single Photon Counting," U.S. Provisional Patent Application Ser. No. 62/889,999, entitled "Photodetector Architectures for Efficient Fast-Gating," U.S. Provisional Patent Application Ser. No. 62/906,620, entitled "Photodetector Systems with Low-Power Time-To-Digital Converter Architectures," U.S. Provisional Patent Application Ser. No. 62/979,866 entitled "Optical Module Assemblies," U.S. Provisional Patent Application Ser. No. 62/992,486 entitled "Laser Diode Driver Circuit with Adjustable Turn-Off and Turn-On Current Slew Rates," U.S. Provisional Patent Application Ser. No. 62/992,491 entitled "Multiplexing Techniques for Interference Reduction in Time-Correlated Signal Photon Counting," U.S. Provisional Patent Application Ser. No. 62/992,493 entitled "SPAD Bias Compensation," U.S. Provisional Patent Application Ser. No. 62/992,497 entitled "Measurement Window Calibration for Detection of Temporal Point Spread Function," U.S. Provisional Patent Application Ser. No. 62/992,499 entitled "Techniques for Determining Impulse Response of SPAD and TDC Systems," U.S. Provisional Patent Application Ser. No. 62/992,502 entitled "Histogram Based Code Density Characterization and Correction in Time-Correlated Single Photon Counting," U.S. Provisional Patent Application Ser. No. 62/992,506 entitled "Selectable Resolution Modes in an Optical Measurement System," U.S. Provisional Patent Application Ser. No. 62/992,510 entitled "Hierarchical Bias Generation for Groups of SPAD Detectors," U.S. Provisional Patent Application Ser. No. 62/992,512 entitled "Detection and Removal of Motion Artifacts in a Wearable Optical Measurement System," U.S. Provisional Patent Application Ser. No. 62/992,526 entitled "Dynamic Range Improvement from Highly Parallel Arrays and SPADs," U.S. Provisional Patent Application Ser. No. 62/992,529 entitled "Single-Photon Avalanche Diode (SPAD) Bias Constant Charge," U.S. Provisional Patent Application Ser. No. 62/992,536 entitled "Calibration of SPAD ToF Systems Based on Per Pixel Dark Count Rate," U.S. Provisional Patent Application Ser. No. 62/992,543 entitled "Estimation of Source-Detector Separation in an Optical Measurement System," U.S. Provisional Patent Application Ser. No. 62/992,550 entitled "Wearable Module for an Optical Measurement or Hybrid Technology Neural Recording System Where the Module Assemblies are Configured for Tiling Multiple Modules Together for Targeted and/or Complete Head Coverage," U.S. Provisional Patent Application Ser. No. 62/992,552 entitled "Wearable Devices for a Brain Computer Interface (BCI) System Where the Wearable Device Includes Conforming Headset Fixation," U.S. Provisional Patent Application Ser. No. 62/992,555 entitled "Integrated Detector Assemblies for a Wearable Module of an Optical Measurement System," U.S. Provisional Patent Application Ser. No. 62/992,559 entitled "Integrated Detector Assemblies for a Wearable Module of an Optical Measurement Where the Detector Assemblies Include Spring Loaded Light Pipes," and U.S. Provisional Patent Application Ser. No. 62/992,567 entitled "Integrated Light Source Assembly with Laser Coupling for a Wearable Optical Measurement System," which are all expressly incorporated herein by reference.

The brain interface assembly 14b includes a head-worn unit 22b that is configured for being applied to the user 12, and in this case, worn on the head of the user 12; and an auxiliary non-head-worn unit 24b (e.g., worn on the neck, shoulders, chest, or arm). Alternatively, the functionality of the unit 24b may be incorporated into the head-worn unit 22b, as described below. The auxiliary non-head-worn unit 24b may be coupled to the head-worn unit 22b via a wired connection 26 (e.g., electrical wires). Alternatively, the brain interface assembly 14b may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22b and the auxiliary unit 24b.

The head-worn unit 22b includes one or more light sources 48 configured for generating light pulses. The light source(s) 48 may be configured for generating one or more light pulses at one or more wavelengths that may be applied to a desired target (e.g., a target within the brain). The light source(s) 48 may be implemented by any suitable combination of components. For example, light source(s) 48 described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (mLED), and/or any other suitable laser or light source.

The head-worn unit 22b includes a plurality of photodetector units 50, e.g., comprising single-photon avalanche diodes (SPADs) configured for detecting a single photon (i.e., a single particle of optical energy) in each of the light pulses. For example, an array of these sensitive photodetector units can record photons that reflect off of tissue within the brain in response to application of one or more of the light pulses generated by the light sources 48. Based on the time it takes for the photons to be detected by the photodetector units, neural activity and other attributes of the brain can be determined or inferred.

Photodetector units that employ the properties of a SPAD are capable of capturing individual photons with very high time-of-arrival resolution (a few tens of picoseconds). When photons are absorbed by a SPAD, their energy frees bound charge carriers (electrons and holes) that then become free-carrier pairs. In the presence of an electric field created by a reverse bias voltage applied to the diode, these free-carriers are accelerated through a region of the SPAD, referred to as the multiplication region. As the free carriers travel through the multiplication region, they collide with other carriers bound in the atomic lattice of the semiconductor, thereby generating more free carriers through a process called impact ionization. These new free-carriers also become accelerated by the applied electric field and generate yet more free-carriers. This avalanche event can be detected and used to determine an arrival time of the photon. In order to enable detection of a single photon, a SPAD is biased with a reverse bias voltage having a magnitude greater than the magnitude of its breakdown voltage, which is the bias level above which free-carrier generation can become self-sustaining and result in a runaway avalanche. This biasing of the SPAD is referred to as arming the device. When the SPAD is armed, a single free carrier pair created by the absorption of a single photon can create a runaway avalanche resulting in an easily detectable macroscopic current.

It will be recognized that in some alternative embodiments, the head-worn unit 22b may include a single light source 48 and/or single photodetector unit 50. For example, brain interface system 14b may be used for controlling a single optical path and for transforming photodetector pixel measurements into an intensity value that represents an optical property of a brain tissue region. In some alternative embodiments, the head-worn unit 22b does not include individual light sources. Instead, a light source configured to generate the light that is detected by the photodetector may be included elsewhere in the brain interface system 14b. For example, a light source may be included in the auxiliary unit 24b.

The head-worn unit 22b further comprises a support housing structure 52 containing the light source(s) 48, photodetector units 50, and other electronic or optical components. As will be described in further detail below, the support housing structure 52 may be shaped, e.g., have a banana, headband, cap, helmet, beanie, other hat shape, or other shape adjustable and conformable to the user's head, such that the photodetector units 50 are in close contact with the outer skin of the head, and in this case, the scalp of the user 12. The support housing structure 52 may be made out of any suitable cloth, soft polymer, plastic, hard shell, and/or any other suitable material as may serve a particular implementation.

While brain interface system 14b shows one head-word unit 22b, any suitable number of head-worn units 22b may be used, for instance at different locations on the head.

The auxiliary unit 24b comprises the housing 36 containing the controller 38 and the processor 40. The controller 38 is configured for controlling the operational functions of the head-worn unit 22b, whereas the processor 40 is configured for processing the photons acquired by the head-worn unit 22b to detect and localize the brain activity of the user 12, as well as to determine the mental state of the user 12 based on the brain activity of the user 12 if not performed by other processing units in the system 10b. The auxiliary unit 24b may additionally include a power supply (which if head-worn, may take the form of a rechargeable or non-chargeable battery), a control panel with input/output functions, a display, and memory. Alternatively, power may be provided to the auxiliary unit 24b wirelessly (e.g., by induction).

The functionalities of the sensory input device/product 16, peripheral device 18, (along with the mixing container 19 (shown in FIG. 1), and database, server, or cloud structure 20 may be the same as described above with respect to the non-invasive product customization system 10 of FIG. 1.

The peripheral device 18 is coupled to the auxiliary unit 24b of the brain interface assembly 14b via a wireless connection 42 (e.g., wireless radio frequency (RF) signals (e.g., Bluetooth, Wifi, cellular, etc.) or optical links (e.g., fiber optic or infrared (IR)) for communicating between the peripheral device 18 and the brain interface assembly 14b. The peripheral device 18 is also coupled to the sensory input device 16a via a wireless connection 44 (e.g., wireless radio frequency (RF) signals (e.g., Bluetooth, Wifi, cellular, etc.) or optical links (e.g., fiber optic or infrared (IR)) for communicating between the peripheral device 18 and the sensory input device 16a. Alternatively, wired connections between the peripheral device 18 and the brain interface assembly 14b and/or the sensory input device 16a may be used. Alternatively or optionally, the product 16b may simply be in the vicinity of the user 12 to provide a natural path 48 in the ambient environment through which the user 12 may sense the product 16b.

The database, server, or cloud structure 20 may be coupled to the auxiliary unit 24b of the brain interface assembly 14b (and/or the peripheral device 18) via a wireless connection 46 (e.g., wireless radio frequency (RF) signals (e.g., Bluetooth, Wifi, cellular, etc.) or optical links (e.g., fiber optic or infrared (IR)) for communicating between the database, server, or cloud structure 20 and the brain interface assembly 14b and peripheral device 18. Alternatively, a wired connection between the database, server, or cloud structure 20 and the auxiliary unit 24b of the brain interface assembly 14b and/or the peripheral device 18 may be used.

Referring now to FIGS. 7A-7D, different embodiments of the brain interface assembly 14b will be described. Such brain interface assemblies 14b may communicate wirelessly or via wire with the peripheral device 18, the sensory input device/product 16, and database, server, cloud structure 20, as described above. Each of the brain interface assemblies 14b described below comprises a head-worn unit 22b having a plurality of photodetector units 50 and a support housing structure 52 in which the photodetector units 50 are embedded. Each of the photodetector units 50 may comprise, e.g., a SPAD, voltage sources, capacitors, switches, and any other circuit components (not shown) required to detect photons. Each of the brain interface assemblies 14b may also comprise one or more light sources (not shown) for generating light pulses, although the source of such light may be derived from ambient light in some cases. Each of brain interface assemblies 14b may also comprise a control/processing unit 54, such as, e.g., a control circuit, time-to-digital (TDC) converter, and signal processing circuit for controlling the operational functions of the photodetector units 50 and any light source(s), and processing the photons acquired by photodetector units 50 to detect and localize the brain activity of the user 12. As will be described in further detail below, the control/processing unit 54 may be contained in the head-worn unit 22b or may be incorporated into a self-contained auxiliary unit. As will be set forth below, the support housing structure 52 may be shaped, e.g., have a banana, headband, cap, helmet, beanie, other hat shape, or other shape adjustable and conformable to the user's head, such that the photodetector units 50 are in close contact with the outer skin of the head, and in this case, the scalp of the user 12.

Figure 7A:
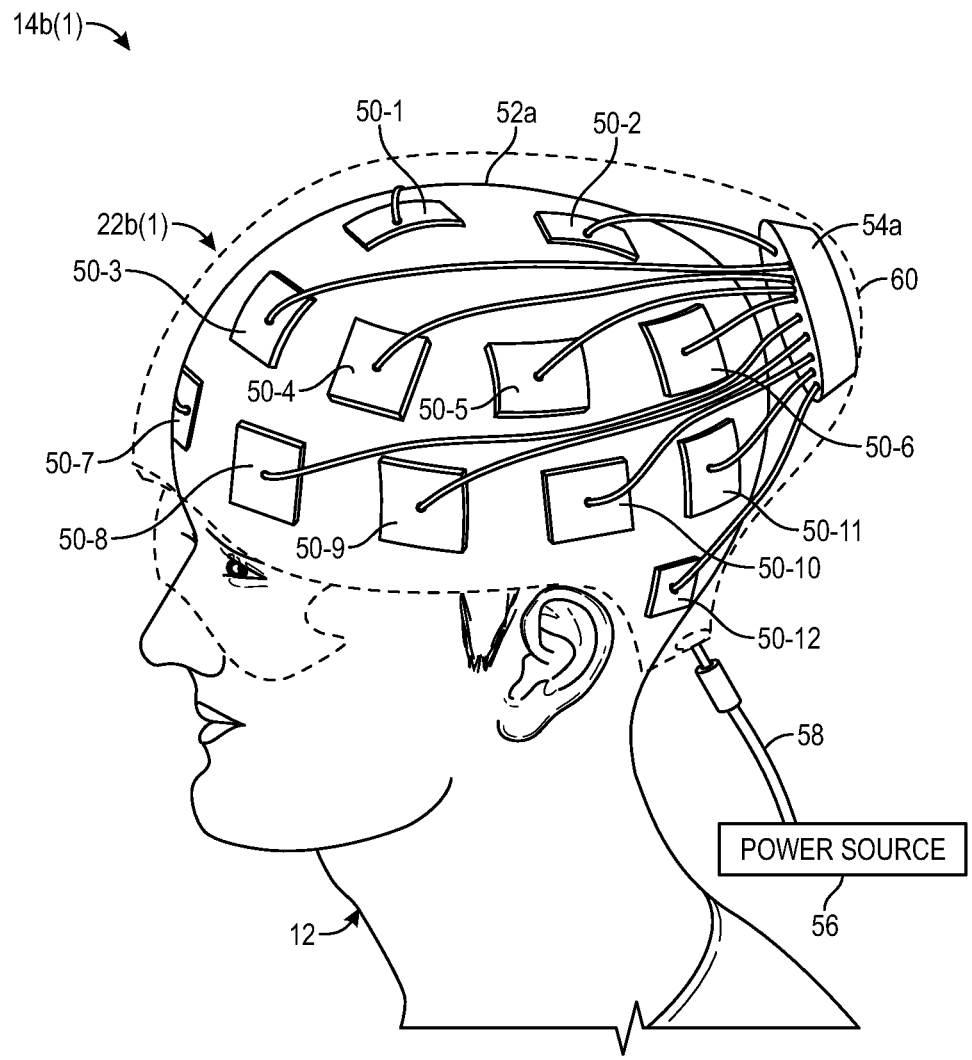
FIGS. 7A-7D illustrate exemplary non-invasive wearable devices as used with the system of FIG. 6.

As shown in FIG. 7A, a brain interface assembly 14b(1) comprises a head-worn unit 22b(1) and a power source 56 coupled to the head-worn unit 22b(1) via a power cord 58. The head-worn unit 22b(1) includes the photodetector units 50 (shown as 50-1 through 50-12) and a control/processing unit 54a. The head-worn unit 22b(1) further includes a support housing structure 52a that takes a form of a cap that contains the photodetector units 50 and control/processing unit 54a. The material for the cap 52a may be selected out of any suitable cloth, soft polymer, plastic, hard shell, and/or any other suitable material as may serve a particular implementation. The power source 56 may be implemented by a battery and/or any other type of power source configured to provide operating power to the photodetector units 50, control/processing unit 54a, and any other component included within the brain interface assembly 22b(1) via the power cord 58. The head-worn unit 22b(1) optionally includes a crest or other protrusion 60 formed in the cap 52a for providing means of carrying/housing a control/processing unit 54a.

Figure 7B:
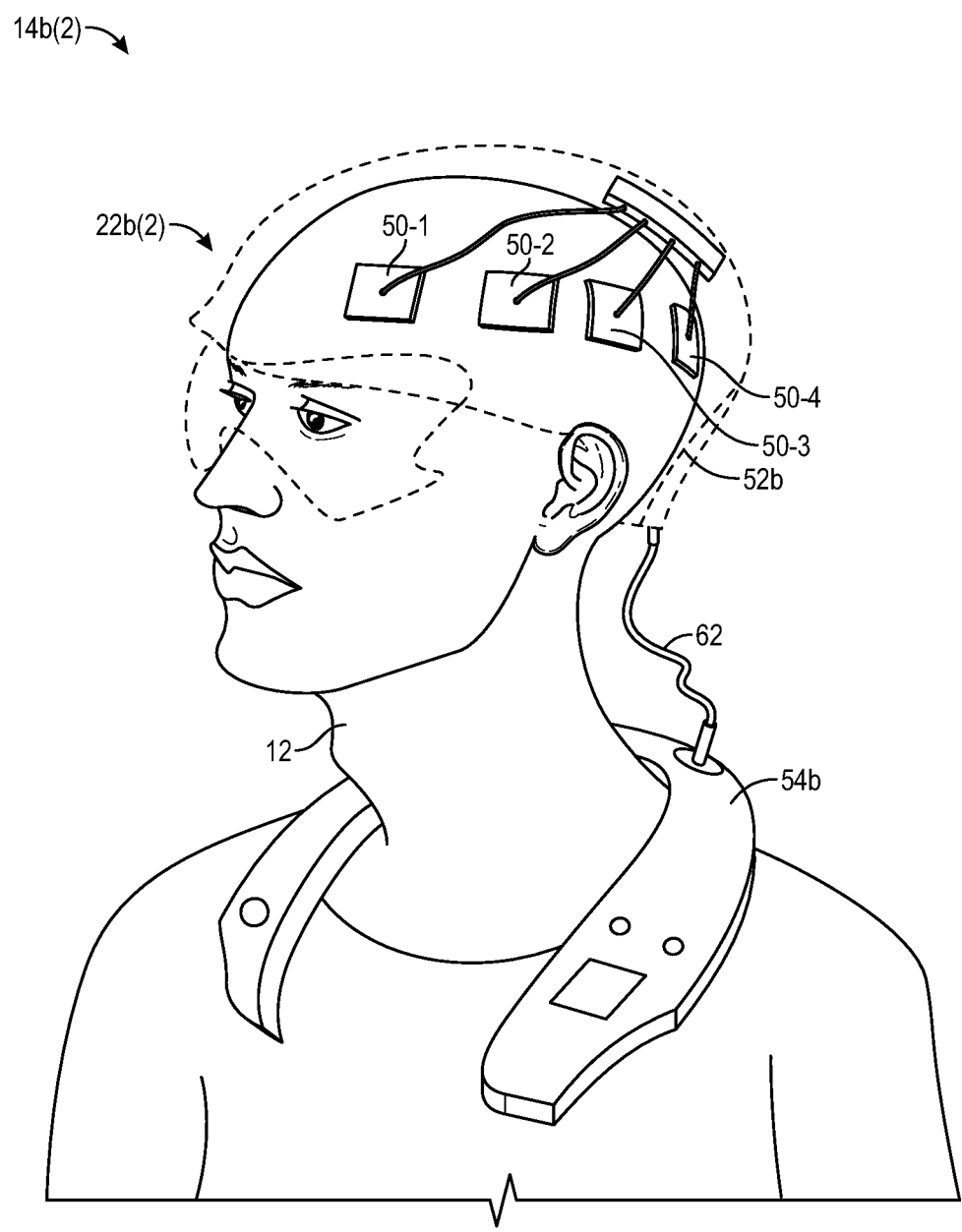

As shown in FIG. 7B, a brain interface assembly 14b(2) comprises a head-worn unit 22b(2) and a control/processing unit 54b coupled to the head-worn unit 22b(2) via a wired connection 62. The head-worn unit 22b(2) includes the photodetector units 50 (shown as 50-1 through 50-4), and a support housing structure 52b that takes a form of a helmet containing the photodetector units 50. The material for the helmet 52b may be selected out of any suitable polymer, plastic, hard shell, and/or any other suitable material as may serve a particular implementation. Unlike the control/processing unit 54a of the brain interface assembly 14b(1) illustrated in FIG. 7A, which is contained in the head-worn unit 22b(1), the control/processing unit 54b is self-contained, and may take the form of a garment (e.g., a vest, partial vest, or harness) for being worn on the shoulders of the user 12. The self-contained control/processing unit 54b may additionally include a power supply (which if head-worn, may take the form of a rechargeable or non-chargeable battery), a control panel with input/output functions, a display, and memory. Alternatively, power may be provided to the self-contained control/processing unit 54b wirelessly (e.g., by induction).

Figure 7C:
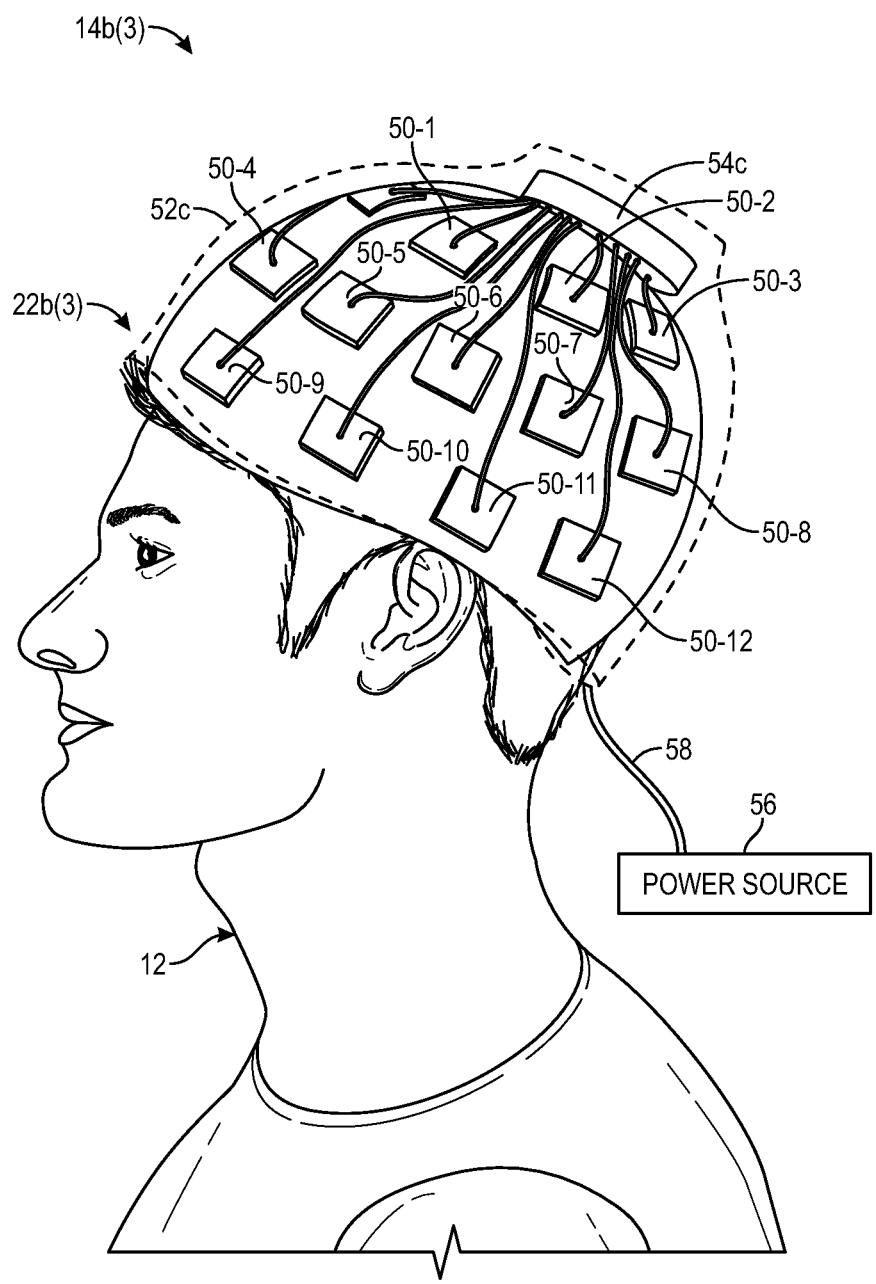

As shown in FIG. 7C, a brain interface assembly 14b(3) comprises a head-worn unit 22b(3) and a power source 56 coupled to the head-worn unit 22b(3) via a power cord 74. The head-worn unit 22b(3) includes the photodetector units 50 (shown as 50-1 through 50-12) and a control/processing unit 54c. The head-worn unit 22b(3) further includes a support housing structure 52c that takes a form of a beanie that contains the photodetector units 50 and control/processing unit 54c. The material for the beanie 52c may be selected out of any suitable cloth, soft polymer, plastic, and/or any other suitable material as may serve a particular implementation. The power source 56 may be implemented by a battery and/or any other type of power source configured to provide operating power to the photodetector units 50, control/processing unit 54c, and any other component included within the brain interface assembly 22b(3) via a wired connection 58.

Figure 7D:
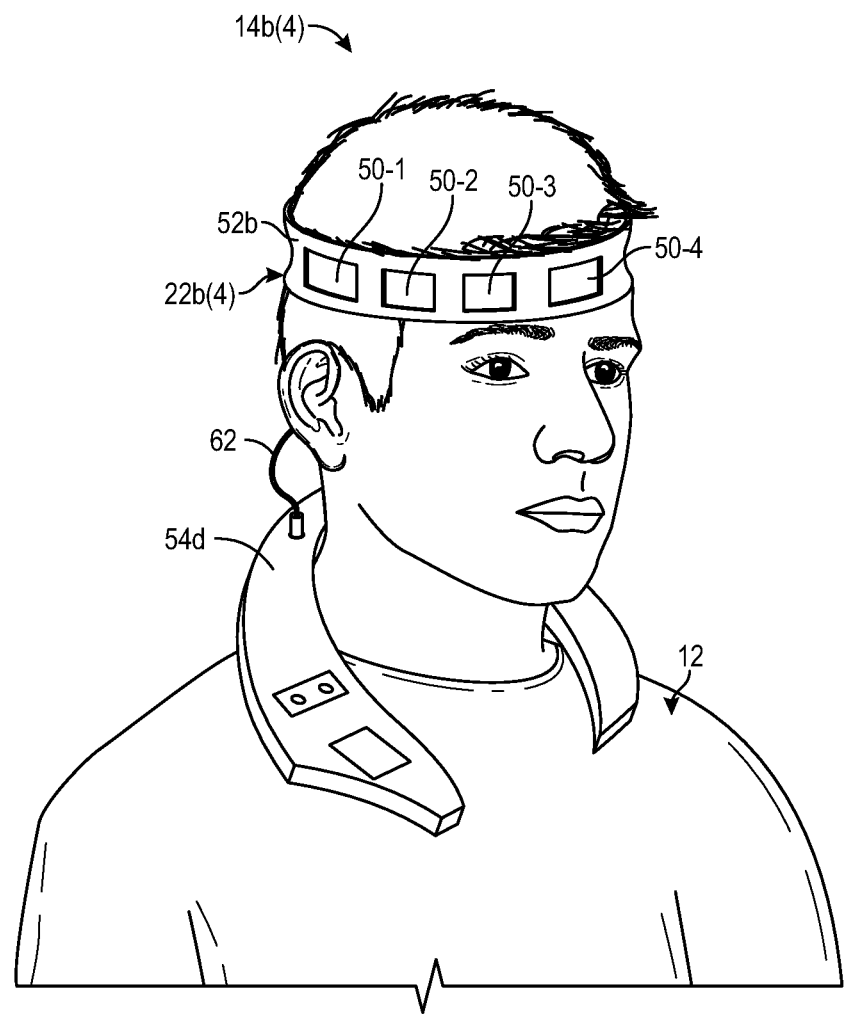

As shown in FIG. 7D, a brain interface assembly 14b(4) comprises a head-worn unit 22b(4) and a control/processing unit 54d coupled to the head-worn unit 22b(4) via a wired connection 62. The head-worn unit 22b(4) includes the photodetector units 50 (shown as 50-1 through 50-4), and a support housing structure 52d that takes a form of a headband containing the photodetector units 50. The material for the headband 52d may be selected out of any suitable cloth, soft polymer, plastic, hard shell, and/or any other suitable material as may serve a particular implementation. The control/processing unit 54d is self-contained, and may take the form of a garment (e.g., a vest, partial vest, or harness) for being worn on the shoulders of the user 12. The self-contained control/processing unit 54d may additionally include a power supply (which if head-worn, may take the form of a rechargeable or non-chargeable battery), a control panel with input/output functions, a display, and memory. Alternatively, power may be provided to the self-contained control/processing unit 54d wirelessly (e.g., by induction).

Figure 8:
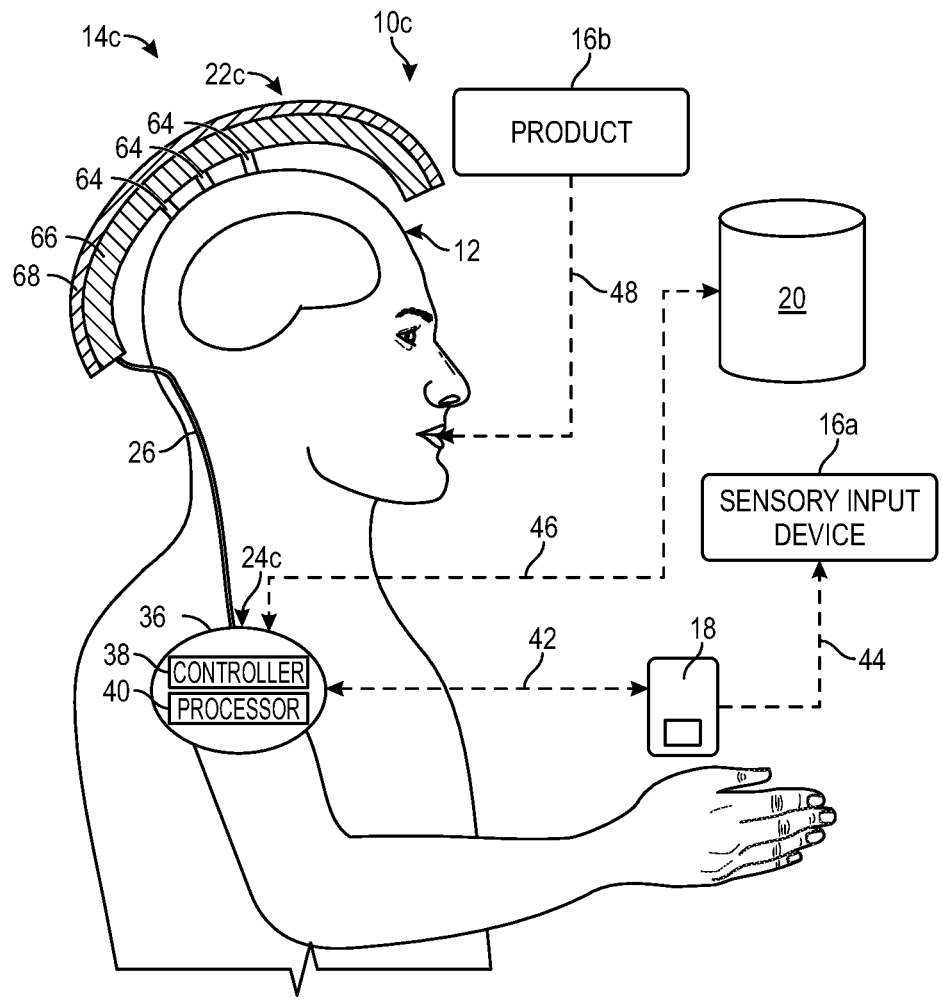
FIG. 8 is a view of still another physical specific embodiment of the non-invasive product formulization system of FIG. 1.

Referring to FIG. 8, a physical implementation of one embodiment of a non-invasive product customization system 10c will now be described. The system 10c comprises a magnetically-based non-invasive brain interface assembly 14c, which may, e.g., incorporate any one or more of the neural activity detection technologies described in U.S.

patent application Ser. No. 16/428,871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418,500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(S)," (now U.S. Pat. No. 10,627,460), U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. Provisional Patent Application Ser. No. 62/858,636, entitled "Integrated Magnetometer Arrays for Magnetoencephalography (MEG) Detection Systems and Methods," U.S. Provisional Patent Application Ser. No. 62/836,421, entitled "Systems and Methods for Suppression of Non-Neural Interferences in Magnetoencephalography (MEG) Measurements," U.S. Provisional Patent Application Ser. No. 62/842,818 entitled "Active Shield Arrays for Magnetoencephalography (MEG)," U.S. Provisional Patent Application Ser. No. 62/926,032 entitled "Systems and Methods for Multiplexed or Interleaved Operation of Magnetometers," U.S. Provisional Patent Application Ser. No. 62/896,929 entitled "Systems and Methods having an Optical Magnetometer Array with Beam Splitters," U.S. Provisional Patent Application Ser. No. 62/960,548 entitled "Methods and Systems for Fast Field Zeroing for Magnetoencephalography (MEG)," U.S. Provisional Patent Application Ser. No. 62/967,787 entitled "Single Controller for Wearable Sensor Unit that Includes an Array Of Magnetometers," U.S. Provisional Patent Application Ser. No. 62/967,797 entitled "Systems and Methods for Measuring Current Output By a Photodetector of a Wearable Sensor Unit that Includes One or More Magnetometers," U.S. Provisional Patent Application Ser. No. 62/967,803 entitled "Interface Configurations for a Wearable Sensor Unit that Includes One or More Magnetometers," U.S. Provisional Patent Application Ser. No. 62/967,804 entitled "Systems and Methods for Concentrating Alkali Metal Within a Vapor Cell of a Magnetometer Away from a Transit Path of Light," U.S. Provisional Patent Application Ser. No. 62/967,813 entitled "Magnetic Field Generator for a Magnetic Field Measurement System," U.S. Provisional Patent Application Ser. No. 62/967,818 entitled "Magnetic Field Generator for a Magnetic Field Measurement System," U.S. Provisional Patent Application Ser. No. 62/967,823 entitled "Magnetic Field Measurement Systems Including a Plurality of Wearable Sensor Units Having a Magnetic Field Generator," U.S. Provisional Patent Application Ser. No. 62/975,709 entitled "Self-Calibration of Flux Gate Offset and Gain Drift To Improve Measurement Accuracy of Magnetic Fields from the Brain Using a Wearable System," U.S. Provisional Patent Application Ser. No. 62/975,693 entitled "Nested and Parallel Feedback Control Loops for Ultra-Fine Measurements of Magnetic Fields from the Brain Using a Wearable MEG System," U.S. Provisional Patent Application Ser. No. 62/975,719 entitled "Estimating the Magnetic Field at Distances from Direct Measurements to Enable Fine Sensors to Measure the Magnetic Field from the Brain Using a Wearable System," U.S. Provisional Patent Application Ser. No. 62/975,723 entitled "Algorithms that Exploit Maxwell's Equations and Geometry to Reduce Noise for Ultra-Fine Measurements of Magnetic Fields from the Brain Using a Wearable MEG System," U.S. Provisional Patent Application Ser. No. 62/975,727 entitled "Optimal Methods to Feedback Control and Estimate Magnetic Fields to Enable a Wearable System to Measure Magnetic Fields from the Brain," and U.S. Provisional Patent Application Ser. No. 62/983,406 entitled "Two Level Magnetic Shielding of Magnetometers," which are all expressly incorporated herein by reference.

The brain interface assembly 14c includes a magnetoencephalography (MEG) head-worn unit 22c that is configured for being applied to the user 12, and in this case, worn on the head of the user 12; and an auxiliary non-head-worn unit 24c (e.g., worn on the neck, shoulders, chest, or arm). Alternatively, the functionality of the unit 24c may be incorporated into the head-worn unit 22c, as described below. The auxiliary non-head-worn unit 24c may be coupled to the head-worn unit 22c via a wired connection 26 (e.g., electrical wires). Alternatively, the brain interface assembly 14c may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22c and the auxiliary unit 24c.

The head-worn unit 22c includes a plurality of optically pumped magnetometers (OPMs) 64 or other suitable magnetometers to measure biologically generated magnetic fields from the brain of the user 12 and a passive shield 66 (and/or flux concentrators). By placing the passive shield 66 over the head of the user 12, the ambient background magnetic field arising from areas outside the passive shield 66 is greatly decreased and the magnetometers 64 can measure or detect magnetic fields from activity occurring in the brain of the user 12 due to the reduction in the ambient background magnetic field.

An OPM is an optical magnetometry system used to detect a magnetic field that propagates through the human head. Optical magnetometry can include the use of optical methods to measure a magnetic field with very high accuracy—on the order of $1\times10^{-15}$ Tesla. Of particular interest for their high-sensitivity, an OPM can be used in optical magnetometry to measure weak magnetic fields. (The Earth's magnetic field is typically around 50 micro Tesla). In at least some systems, the OPM has an alkali vapor gas cell that contains alkali metal atoms in a combination of gas, liquid, or solid states (depending on temperature). The gas cell may contain a quenching gas, buffer gas, or specialized anti-relaxation coatings or any combination thereof. The size of the gas cells can vary from a fraction of a millimeter up to several centimeters, allowing the practicality of OPMs to be used with wearable non-invasive brain interface devices.

The head-worn unit 22c further comprises a support housing structure 68 containing the OPMs 64, passive shield 66, and other electronic or magnetic components. As will be described in further detail below, the support housing structure 68 may be shaped, e.g., have a banana, headband, cap, helmet, beanie, other hat shape, or other shape adjustable and conformable to the user's head, such that the OPMs 64 are in close contact with the outer skin of the head, and in this case, the scalp of the user 12. The support housing structure 68 may be made out of any suitable cloth, soft polymer, plastic, hard shell, and/or any other suitable material as may serve a particular implementation.

The auxiliary unit 24c comprises the housing 36 containing the controller 38 and the processor 40. The controller 38 is configured for controlling the operational functions of the head-worn unit 22c, whereas the processor 40 is configured for processing the magnetic fields detected by the head-worn unit 22c to detect and localize the brain activity of the user 12, as well as to determine the mental state of the user 12 based on the brain activity of the user 12 if not performed by other processing units in the system 10c. The auxiliary unit 24c may additionally include a power supply (which if head-worn, may take the form of a rechargeable or non-chargeable battery), a control panel with input/output functions, a display, and memory. Alternatively, power may be provided to the auxiliary unit 24c wirelessly (e.g., by induction).

The functionalities of the sensory input device/product 16, peripheral device 18 (along with the mixing container 19 (shown in FIG. 1), and database, server, or cloud structure 20 may be the same as described above with respect to the non-invasive product customization system 10 of FIG. 1.

The peripheral device 18 is coupled to the auxiliary unit 24c of the brain interface assembly 14c via a wireless connection 42 (e.g., wireless radio frequency (RF) signals (e.g., Bluetooth, Wifi, cellular, etc.) or optical links (e.g., fiber optic or infrared (IR)) for communicating between the peripheral device 18 and the brain interface assembly 14c. The peripheral device 18 is also coupled to the sensory input device 16a via a wireless connection 44 (e.g., wireless radio frequency (RF) signals (e.g., Bluetooth, Wifi, cellular, etc.) or optical links (e.g., fiber optic or infrared (IR)) for communicating between the peripheral device 18 and the sensory input device 16a. Alternatively, wired connections between the peripheral device 18 and the brain interface assembly 14c and/or the sensory input device 16a may be used. Alternatively or optionally, the product 16b may simply be in the vicinity of the user 12 to provide a natural path 48 in the ambient environment through which the user 12 may sense the product 16b.

The database, server, or cloud structure 20 may be coupled to the auxiliary unit 24c of the brain interface assembly 14c (and/or the peripheral device 18) via a wireless connection 46 (e.g., wireless radio frequency (RF) signals (e.g., Bluetooth, Wifi, cellular, etc.) or optical links (e.g., fiber optic or infrared (IR)) for communicating between the database, server, or cloud structure 20 and the brain interface assembly 14c and peripheral device 18. Alternatively, a wired connection between the database, server, or cloud structure 20 and the auxiliary unit 24c of the brain interface assembly 14c and/or the peripheral device 18 may be used.

Figure 9A:
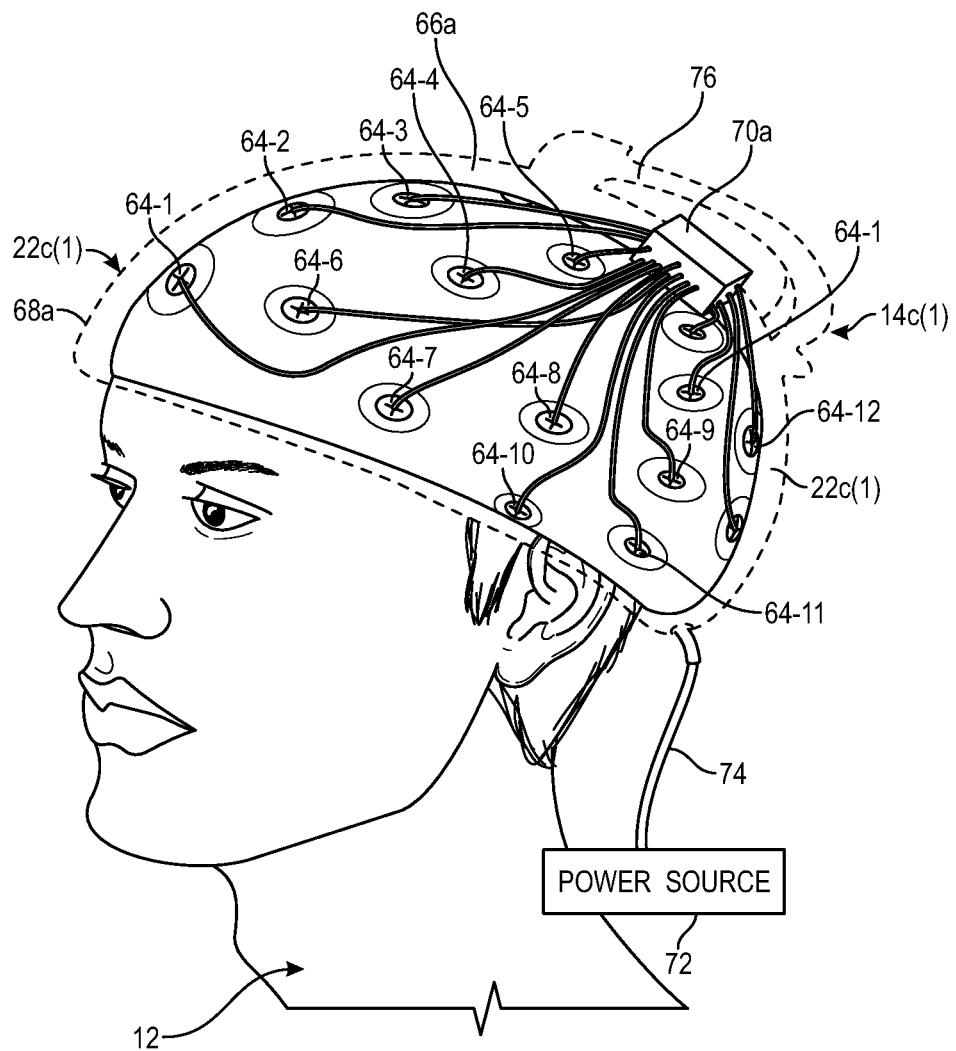
FIGS. 9A-9C illustrate exemplary non-invasive wearable devices as used with the system of FIG. 8.
Figure 9B:
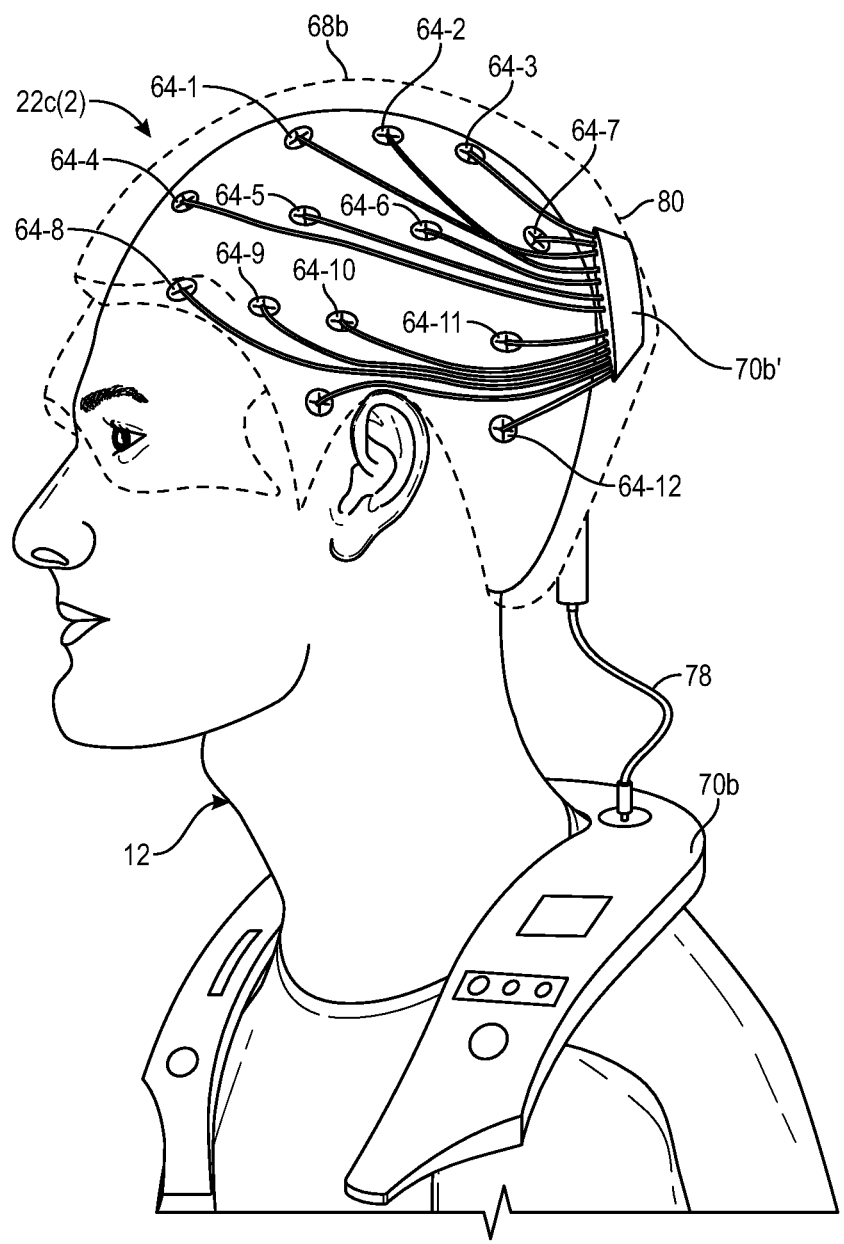
Figure 9C:
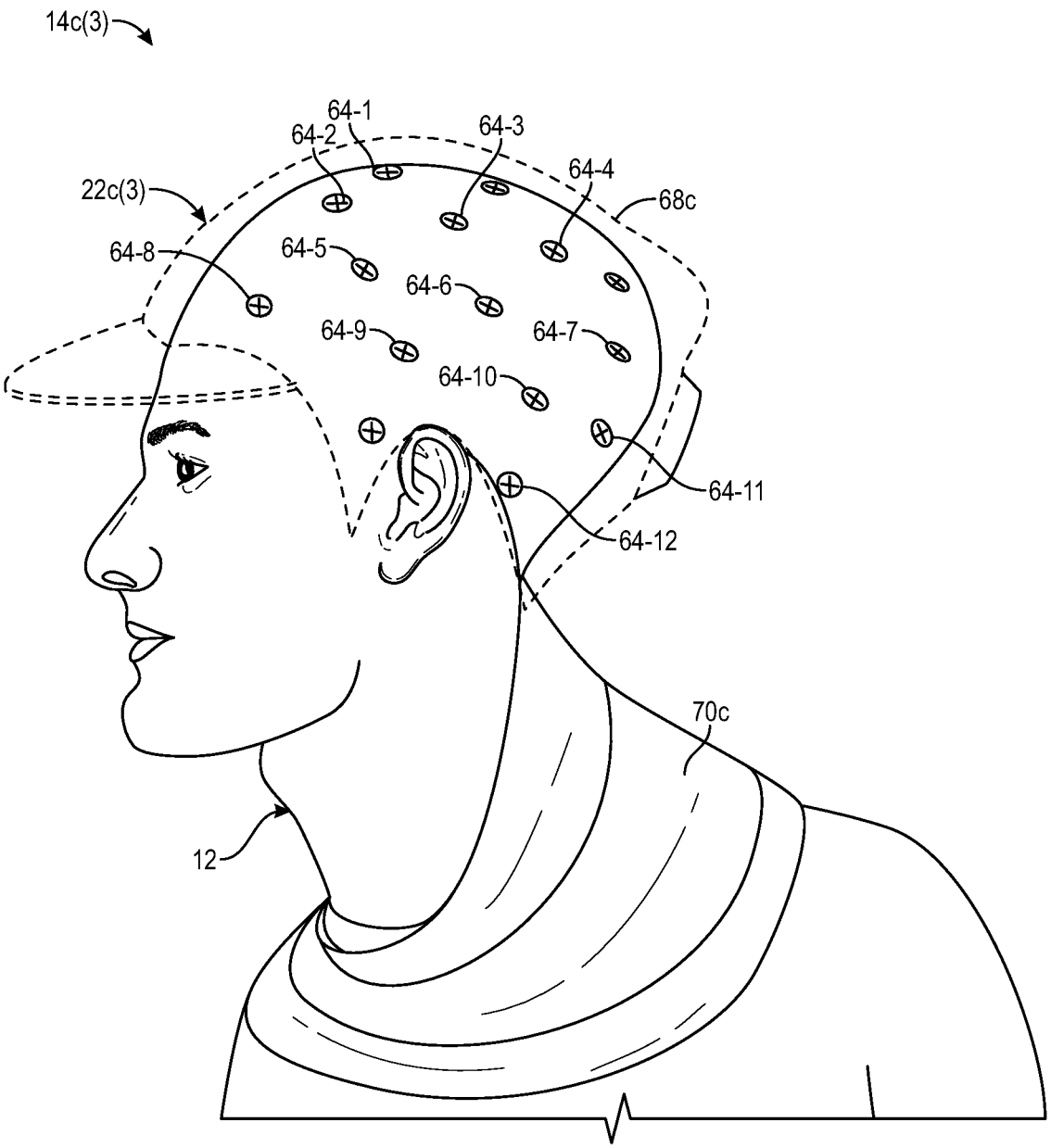

Referring now to FIGS. 9A-9C, different embodiments of the brain interface assembly 14c will be described. Such brain interface assemblies 14c may communicate wirelessly or via wire with the peripheral device 18, sensory input device/product 16, and database, server, cloud structure 20, as described above. Each of the brain interface assemblies 14c described below comprises a head-worn unit 22c having a plurality of OPMs 64, a passive shield 66, and a support housing structure 68 in which the OPMs 64 and passive shield 66 are embedded. Each of brain interface assemblies 14c may also comprise a control/processing unit 70 for controlling the operational functions of the OPMs 64, and processing the magnetic fields detected by the OPMs 64 to detect and localize the brain activity of the user 12. As will be described in further detail below, the control/processing unit 70 may be contained in the head-worn unit 22c or may be incorporated into a self-contained auxiliary unit. As will be set forth below, the support housing structure 68 may be shaped, e.g., have a banana, headband, cap, helmet, beanie, other hat shape, or other shape adjustable and conformable to the user's head, such that the magnetometers 64 are in close contact with the outer skin of the head, and in this case, the scalp of the user 12.

As shown in FIG. 9A, a brain interface assembly 14c(1) comprises a head-worn unit 22c(1) and a power source 72 coupled to the head-worn unit 22c(1) via a wired connection 74. The head-worn unit 22c(1) includes the OPMs 64 (shown as 64-1 through 64-12) and a control/processing unit 70a. The head-worn unit 22c(1) further includes a support housing structure 68a that takes a form of a helmet that contains the OPMs 64, passive shield 66, and control/processing unit 70a. The material for the helmet 68a may be selected out of any suitable cloth, soft polymer, plastic, hard shell, and/or any other suitable material as may serve a particular implementation. The power source 72 may be implemented by a battery and/or any other type of power source configured to provide operating power to the magnetometers 64, control/processing unit 70a, and any other component included within the brain interface assembly 22c(1) via the wired connection 74. The head-worn unit 22c(1) optionally includes a handle 76 affixed to the helmet 68a for providing a convenient means of carrying the head-worn unit 22c(1).

As shown in FIG. 9B, a brain interface assembly 14c(2) comprises a head-worn unit 22c(2) and a control/processing unit 70b coupled to the head-worn unit 22b(2) via a wired connection 78. The head-worn unit 22c(2) includes the OPMs 64 (shown as 64-1 through 64-12), and a support housing structure 68b that takes a form of a helmet that contains the OPMs 64 and passive shield 66. The material for the helmet 68b may be selected out of any suitable cloth, soft polymer, plastic, hard shell, and/or any other suitable material as may serve a particular implementation. Unlike the control/processing unit 70a of the brain interface assembly 14c(1) illustrated in FIG. 9A, which is contained in the head-worn unit 22c(1), the control/processing unit 70b is self-contained, and may take the form of a garment (e.g., a vest, partial vest, or harness) for being worn on the shoulders of the user 12. The self-contained control/processing unit 70b may additionally include a power supply (which if head-worn, may take the form of a rechargeable or non-chargeable battery), a control panel with input/output functions, a display, and memory. Alternatively, power may be provided to the self-contained control/processing unit 70b wirelessly (e.g., by induction). The head-worn unit 22c(1) optionally includes a crest or other protrusion 80 formed in the helmet 68b for providing means of carrying a control/processing unit 70b'.

As shown in FIG. 9C, a brain interface assembly 14c(3) comprises a head-worn unit 22c(3) and a control/processing unit 70c. The head-worn unit 22c(3) includes the OPMs 64 (shown as 64-1 through 64-12), and a support housing structure 68c that takes a form of a baseball cap that contains the OPMs 64 and passive shield 66. The material for baseball cap 68c may be selected out of any suitable cloth, soft polymer, plastic, hard shell, and/or any other suitable material as may serve a particular implementation. The control/processing unit 70c is self-contained, and may take the form of a garment (e.g., scarf) for being worn around the neck of the user 12. The self-contained control/processing unit 70c may additionally include a power supply (which if head-worn, may take the form of a rechargeable or non-chargeable battery), a control panel with input/output functions, a display, and memory. Alternatively, power may be provided to the self-contained control/processing unit 70c wirelessly (e.g., by induction).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A non-invasive product customization system, comprising:
   a sensory input device;
   a non-invasive brain interface assembly configured for detecting brain activity of a user; and
   at least one processor configured for instructing the sensory input device to present the product formulation to the user for input into the brain of the user via the sensory nervous system of the user, determining a mental state of the user based on the brain activity detected by the non-invasive brain interface assembly in response to presenting the product formulation to the user, modifying the product formulation within a virtual mixing container based on the determined mental state of the user, determining a negative mental state of the user based on brain activity detected by the non-invasive brain interface assembly when a product formulation is not presented to the user via the sensory input device, and automatically instructing the sensory input device to present the modified product formulation to the user in response to the determined negative mental state of the user in a manner that modulates the negative mental state of the user to promote a positive mental state of the user.

2. The non-invasive product customization system of claim 1, wherein the non-invasive brain interface assembly is an optical measurement assembly.

3. The non-invasive product customization system of claim 1, wherein the non-invasive brain interface assembly is a magnetic measurement assembly.

4. The non-invasive product customization system of claim 1, wherein the product formulation is input into the brain of the user via the olfactory sensory system and/or gustatory sensory system.

5. The non-invasive product customization system of claim 1, wherein the product formulation comprises a formulation of one or more of a fragrance, homeopathic oil for external therapeutic applications, lotion, food, drink, and psychotropic substances.

6. The non-invasive product customization system of claim 1, wherein the mental state comprises one of an emotional state, a cognitive state, and a perceptive state.

7. The non-invasive product customization system of claim 1, wherein the at least one processor is configured for determining a level of the mental state of the user based on the detected brain activity, and modifying the product formulation based on the level of the determined mental state of the user.

8. The non-invasive product customization system of claim 1, wherein the at least one processor is configured for modifying the product formulation by adding a selected ingredient to the product formulation within the virtual mixing container.

9. The non-invasive product customization system of claim 1, wherein the at least one processor is configured for modifying the product formulation by discarding a selected ingredient from the product formulation within the virtual mixing container.

10. The non-invasive product customization system of claim 1, wherein the at least one processor is configured for modifying the product formulation by modifying a dosage of a selected existing ingredient in the product formulation within the virtual mixing container.

11. The non-invasive product customization system of claim 1, wherein the at least one processor is further configured for combining ingredients of the modified product formulation into a final product formulation.

12. The non-invasive product customization system of claim 1, wherein a portion of the at least one processor is contained in the brain interface assembly for determining the mental state of the user based on the detected brain activity, and another portion of the at least one processor is contained in a peripheral device for modifying the product formulation within the virtual mixing container based on the determined mental state of the user.

13. The non-invasive product customization system of claim 1, wherein the non-invasive brain interface assembly is a portable and wearable non-invasive brain interface assembly.

14. A method of customizing a product formulation using a sensory device, a non-invasive brain interface assembly, and at least one processor, comprising:
   detecting brain activity of a user, via the non-invasive brain interface assembly, in response to an input of the product formulation into a brain of the user via the sensory nervous system of the user;
   determining the mental state of the user, using the at least one processor, based on the detected brain activity;
   modifying the product formulation, using the at least one processor, based on the determined mental state of the user;
   subsequently detecting the brain activity of the user when a product formulation is not presented to the user, via the non-invasive brain interface assembly;
   determining a negative mental state of the user based on brain activity subsequently detected by the non-invasive brain interface assembly; and
   automatically instructing the sensory input device to present the modified product formulation to the user in response to the determined negative mental state of the user in a manner that modulates the negative mental state of the user to promote a positive mental state of the user.

15. The method of claim 14, wherein the product formulation is input into the brain of the user via the olfactory sensory system and/or gustatory sensory system.

16. The method of claim 14, wherein the product formulation comprises a formulation of one or more of a fragrance, homeopathic oil for external therapeutic applications, lotion, food, drink, and psychotropic substances.

17. The method of claim 14, wherein the mental state comprises one of an emotional state, a cognitive state, and a perceptive state.

18. The method of claim 14,
   wherein determining the mental state of the user based on the detected brain activity comprises determining a level of the mental state of the user based on the detected brain activity; and wherein the product formulation is modified based on the level of the determined mental state of the user.

19. The method of claim 14, wherein modifying the product formulation comprises adding a selected ingredient to the product formulation.

20. The method of claim 14, wherein modifying the product formulation comprises discarding a selected ingredient from the product formulation.

21. The method of claim 14, wherein modifying the product formulation comprises modifying a dosage of a selected existing ingredient in the product formulation.

22. The method of claim 14, further comprising, combining ingredients of the modified product formulation into a final product formulation via the at least one processor.

23. The non-invasive product customization system of claim 1, wherein the determined negative mental state of the user is one of anxiety and fear, and the positive mental state of the user is one of joy, relaxation, and a cognitive state.

24. The non-invasive product customization system of claim 1, wherein the at least one processor is configured for determining whether the user has been continually in the negative mental state for a certain period of time, and automatically instructing the sensory input device to present the modified product formulation to the user only if the user has been continually in the negative mental state for the certain period of time.

25. The method of claim 14, wherein the determined negative mental state of the user is one of anxiety and fear, and the positive mental state of the user is one of joy, relaxation, and a cognitive state.

26. The method of claim 14, further comprising determining whether the user has been continually in the negative mental state for a certain period of time, and automatically instructing the sensory input device to present the modified product formulation to the user only if the user has been continually in the negative mental state for the certain period of time.

* * * * *